United States Patent [19]
Deckner et al.

[11] Patent Number: 5,989,536
[45] Date of Patent: *Nov. 23, 1999

[54] PERSONAL CLEANSING COMPOSITIONS CONTAINING ALKOXYLATED ETHER AND CATIONIC AMMONIUM SALT FOR DEPOSITION OF ACTIVE AGENT UPON THE SKIN

[75] Inventors: George Endel Deckner, Cincinnati; Richard Loren McManus, West Chester; Dawn Marie French, Cincinnati, all of Ohio

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/629,790

[22] Filed: Apr. 9, 1996

Related U.S. Application Data

[63] Continuation of application No. 08/371,049, Jan. 10, 1995, abandoned, which is a continuation of application No. 08/161,104, Dec. 2, 1993, abandoned, which is a continuation of application No. 08/100,957, Aug. 3, 1993, abandoned.

[51] Int. Cl.$^6$ .............................. A61K 7/48; A61K 7/40
[52] U.S. Cl. ...................... 424/78.05; 514/846; 514/859; 424/78.02; 424/78.06; 424/78.07; 424/78.03
[58] Field of Search .............................. 424/78.02, 78.03, 424/78.06, 78.05, 78.07

[56] References Cited

U.S. PATENT DOCUMENTS

| | | | |
|---|---|---|---|
| 3,920,810 | 11/1975 | Rankin | 424/80 |
| 4,039,501 | 8/1977 | Babcock et al. | 260/30.4 R |
| 4,147,782 | 4/1979 | Klein et al. | 424/230 |
| 4,318,907 | 3/1982 | Kligman et al. | 424/230 |
| 4,355,028 | 10/1982 | Kligman et al. | 424/230 |
| 4,499,069 | 2/1985 | Krafton | 424/66 |
| 4,540,568 | 9/1985 | Trager et al. | 424/81 |
| 4,597,963 | 7/1986 | Deckner | 424/59 |
| 4,599,379 | 7/1986 | Flesher et al. | 524/801 |
| 4,628,078 | 12/1986 | Glover et al. | 526/303.1 |
| 4,673,704 | 6/1987 | Flesher et al. | 524/519 |
| 4,704,436 | 11/1987 | Barabas | 525/326.9 |
| 4,806,345 | 2/1989 | Bhattacharyya | 424/70 |
| 4,835,206 | 5/1989 | Farrar et al. | 524/457 |
| 4,837,019 | 6/1989 | Georgalas et al. | 424/101 |
| 4,849,484 | 7/1989 | Heard | 525/221 |
| 4,885,161 | 12/1989 | Cornell | 424/78 |
| 4,915,940 | 4/1990 | Saitoh et al. | 424/81 |
| 4,929,577 | 5/1990 | Cornell | 514/58 |
| 4,946,670 | 8/1990 | Sebag et al. | 424/63 |
| 4,970,220 | 11/1990 | Chaussee | 514/358 |
| 4,971,800 | 11/1990 | Chess et al. | 424/449 |
| 5,009,969 | 4/1991 | Miller | 424/401 |
| 5,017,367 | 5/1991 | Stojkoski | 424/63 |
| 5,045,317 | 9/1991 | Chess et al. | 424/401 |
| 5,051,260 | 9/1991 | Chess et al. | 424/449 |
| 5,100,660 | 3/1992 | Hawe et al. | 424/78.35 |
| 5,106,609 | 4/1992 | Bolich, Jr. et al. | 424/70.12 |
| 5,221,530 | 6/1993 | Janchitraponveg et al. | 424/70 |
| 5,232,688 | 8/1993 | Ziegler et al. | 424/59 |
| 5,407,958 | 4/1995 | Heath et al. | 514/546 |
| 5,484,597 | 1/1996 | Slautcheff et al. | 424/401 |

FOREIGN PATENT DOCUMENTS

| | | | |
|---|---|---|---|
| 067658 | 6/1982 | European Pat. Off. | A61K 7/00 |
| 228868 | 12/1986 | European Pat. Off. | C08F 226/02 |
| 312208 | 9/1988 | European Pat. Off. | A61K 37/02 |
| 0299758 | 1/1989 | European Pat. Off. | |
| 299758 | 1/1989 | European Pat. Off. | A61K 47/00 |
| 2071745 | 6/1982 | Japan | A61K 9/70 |
| 57091913 | 3/1990 | Japan | A61K 9/70 |
| 2236760 | 10/1990 | United Kingdom | C11D 17/00 |
| 93/07856 | 4/1993 | WIPO | A61K 7/48 |
| 93/07902 | 4/1993 | WIPO | A61K 47/32 |
| 93/07903 | 4/1993 | WIPO | A61K 47/32 |
| WO9307903 | 4/1993 | WIPO | |
| 9310755 | 6/1993 | WIPO | A61K 7/48 |
| 9310756 | 6/1993 | WIPO | A61K 7/48 |
| 94/02176 | 2/1994 | WIPO | A61K 47/32 |

OTHER PUBLICATIONS

Washington Post Health Jun. 12, 1990 pp. 10–12 "It's A Cream . . . Cosmeceutical".

Technical Bulletin—Salcare SC 92 for Cosmetic/Personal Care Applications, Allied Colloids, Suffolk, VA—undated.

Technical Bulletin—Salcare SC91: The Cosmetic Formulator's Choice For Anionic Skin Care Products Allied Colloids, Suffolk, VA—undated.

*Primary Examiner*—Peter F. Kulkosky
*Attorney, Agent, or Firm*—Darryl C. Little

[57] ABSTRACT

The present invention relates to oil-in-water emulsion compositions that are useful for personal cleansing and for depositing an active ingredient upon the skin surface. The active ingredient in these compositions has a solubility parameter from about 7 to about 13. A preferred active ingredient is salicylic acid.

54 Claims, No Drawings

PERSONAL CLEANSING COMPOSITIONS CONTAINING ALKOXYLATED ETHER AND CATIONIC AMMONIUM SALT FOR DEPOSITION OF ACTIVE AGENT UPON THE SKIN This is continuation of application Ser. No. 08/371,049, filed on Jan. 10, 1995, abandoned which is a continuation of application Ser. No. 08/161,104, filed on Dec. 2, 1993, abandoned which is a continuation-in-part of application Ser. No. 08/100,957, filed on Aug. 3, 1993, abandoned.

TECHNICAL FIELD

The present invention relates to personal cleansing compositions which both cleanse the skin and deposit an active ingredient upon the skin during the cleansing process. These cleansing compositions are in the form of oil-in-water emulsions. These compositions are useful for delivering a wide variety of active ingredients. Cleansing compositions containing salicylic acid as the active are highly preferred and are useful for both cleansing the skin and for providing anti-acne and anti-skin wrinkling benefits.

BACKGROUND OF THE INVENTION

There is a continuing interest in providing consumers with personal cleansing compositions which not only cleanse the skin, but which also provide additional skin care benefits. For example, it would be highly desirable to provide products which both thoroughly cleanse the skin and which also deposit various active ingredients upon the skin surface during the cleansing process. These dual goals of cleansing the skin and depositing an active are difficult to achieve from a single product, because the surfactant ingredients typically found in a skin cleansing product tend to inhibit the deposition of actives from the product and also tend to remove the actives which have deposited. Therefore, the need exists to develop compositions which effectively achieve both of these goals of cleansing and deposition.

A significant segment of the population suffers from acne. These individuals have special skin cleansing needs. Acne sufferers need to keep their skin clean to remove dirt, oils, bacteria, and other foreign materials. Acne sufferers also need to treat their skin with various medicaments to both ameliorate exisiting acne lesions and to prevent future acne lesions. Even though cleansing products which contain various active ingredients are known and are targeted to acne sufferers, many of these cleansing products do not effectively deposit therapeutic levels of the active ingredients upon the skin. Therefore, acne sufferers need to use two separate products, namely a cleansing product followed by an anti-acne medicament, to obtain effective anti-acne protection.

Not only acne sufferers have the unmet need of finding products which both cleanse and treat the skin. For example, a significant segment of the population is concerned with skin aging effects, i.e. wrinkling, sagging, age spots, and other age-related skin changes. These individuals also have special skin cleansing needs. These individuals need to keep their skin clean and also need to treat their skin to reduce the aging effects which have already occurred and to prevent or diminish future aging effects from occurring. Furthermore, these individuals also have the need to moisturize their skin. As with acne sufferers, there is again a lack of products which both cleanse and treat the skin, thus necessitaing the use of separate cleansing and treatment products.

A wide variety of active ingredients are currently known for treating various skin conditions. Representative of some of these active ingredients is salicylic acid. Salicylic acid is a well known keratoylic agent which is believed to help remove keratin plugs and to aid the skin's exfoliation process. Salicylic acid is described further in C. Huber et al., Arch. Derm. Res. 257, pp. 293–297, 1977). Salicylic acid is known for its anti-acne benefits and is available in numerous over-the-counter products. See C. Huber et al., Arch. Derm. Res. 257, pp. 293–297, 1977. Salicylic acid is also known for its anti-skin aging benefits. See PCT Patent Application No. 9310755, to Blank et al., published Jun. 10, 1993 and PCT Application No. 9310756, to Blank, published Jun. 10, 1993. However, it is difficult to deliver effective levels of salicylic acid to the skin from conventionl skin cleansing products. This challenge is especially difficult in light of FDA regulations which limit the level of salicylic acid in skin care products to only 2%. See, "Topical Acne Drug Products For Over The Counter Human Use Final Monograph", 21 CFR 333, Aug. 16, 1991. Thus the need exists for developing products which thoroughly cleanse the skin and which also deliver therapeutically effective levels of salicylic acid to the skin within the FDA formulation constraints.

It has been found in the present invention that cleansing compositions in the form of oil-in-water emulsions can be formulated which are useful for both cleansing the skin and depositing effective levels of a wide variety of active ingredients during the cleansing process. It has been found that these emulsions are useful for depositing actives having a solubility parameter from about 7 to about 13. It has also been found that these emulsions are especially useful for depositing salicylic acid.

It is an object of the present invention to provide personal cleansing oil-in-water emulsion compositions which are useful for both cleansing the skin and depositing active ingredients upon the skin surface during the cleansing process.

It is a further object of the present invention to provide compositions which are useful for both cleansing the skin and providing an anti-acne benefit.

It is a further object of the present invention to provide compositions which are useful for both cleansing the skin and providing an anti-skin aging benefit.

It is a further object of the present invention to provide compositions which are useful for both cleansing the skin and for depositing salicylic acid upon the skin surface during the cleansing process.

It is a further object of the present invention to provide methods for cleansing the skin and for depositing active ingredients upon the skin surface.

These and other objects of this invention will become apparent in light of the following disclosure.

SUMMARY OF THE INVENTION

The present invention relates to a personal cleansing oil-in-water emulsion, comprising:

(a) from about 0.05% to about 20% of an active ingredient having a solubility parameter from about 7 to about 13;

(b) from about 0.1% to about 25% of an alkoxylated ether of the formula

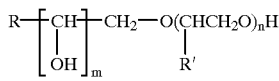

wherein R is selected from the group consisting of H and C1–C30 straight chain or branched chain alkyl, m is an integer from 0 to about 6, R' is selected from the group consisting of methyl and ethyl, and n is an integer from about 3 to about 30; or an alkoxylated diether of the formula

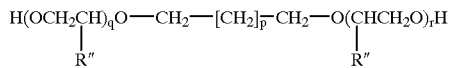

wherein R" is selected from the group consisting of methyl and ethyl, p is an integer from about 1 to about 6, and each q and r are independently selected so that their sum is an integer from about 3 to about 30;
(c) from about 0.05% to about 10% of an emulsifier;
(d) from about 0% to about 10% of a deposition aiding polymer;
(e) from 0% to about 10% of a polymeric thickener; and
(f) from about 25% to about 99.7% water.

In further embodiments the present invention relates to an oil-in-water emulsion composition useful for personal cleansing, comprising:
(a) from about 0.05% to about 20% of salicylic acid;
(b) from about 0.1% to about 25% of an alkoxylated ether of the formula

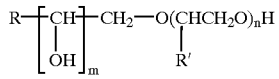

wherein R is selected from the group consisting of H and C1–C30 straight chain or branched chain alkyl, m is an integer from 0 to about 6, R' is selected from the group consisting of methyl and ethyl, and n is an integer from about 3 to about 30; or an alkoxylated diether of the formula

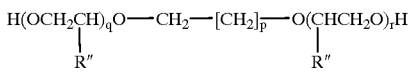

wherein R" is selected from the group consisting of methyl and ethyl, p is an integer from about 1 to about 6, and each q and r are independently selected so that their sum is an integer from about 3 to about 30;
(c) from about 0.05% to about 10% of an emulsifier;
(d) from about 0% to about 10% of a deposition aiding polymer;
(e) from 0% to about 10% of a polymeric thickener; and
(f) from about 25% to about 99.7% water;
wherein said composition has a pH from about 2 to about 7.

In even further embodiments the present invention relates to an oil-in-water emulsion composition useful for personal cleansing, comprising:
(a) from about 0.05% to about 20% of an active ingredient having a solubility parameter from about 7 to about 13;
(b) from about 0.1% to about 25% of an alkoxylated ether of the formula

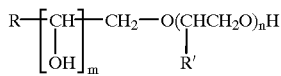

wherein R is selected from the group consisting of H and C1–C30 straight chain or branched chain alkyl, m is an integer from 0 to about 6, R' is selected from the group consisting of methyl and ethyl, and n is an integer from about 3 to about 30; or an alkoxylated diether of the formula

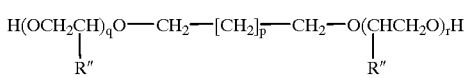

wherein R" is selected from the group consisting of methyl and ethyl, p is an integer from about 1 to about 6, and each q and r are independently selected so that their sum is an integer from about 3 to about 30;
(c) from about 0.05% to about 10% of an emulsifier;
(d) from about 0.1% to about 10% of a deposition aiding polymer which is a mixture of a hydroxy-terminated urethane polymer and a polypropylene glycol wherein the weight/weight ratio of said hydroxy-terminated urethane polymer to said polypropylene glycol is from about 1:1.5 to about 1.5:1;
(e) from 0% to about 10% of a polymeric thickener; and
(f) from about 25% to about 99.7% water.

All percentages and ratios used herein are by weight of the total composition and all measurements made are at 25° C., unless otherwise designated. The invention hereof can comprise, consist of, or consist essentially of, the essential as well as optional ingredients and components described herein.

DETAILED DESCRIPTION OF THE INVENTION

The emulsion compositions of the present invention are useful for cleansing the skin and for depositing an active ingredient onto the skin during the cleansing process. These compositions are in the form of oil-in-water emulsions whereby the oil phase and the water phase can contain, in addition to the essential components described herein, a wide variety of ingredients known in the art. The active ingredients are deposited to the skin from the oil phase of the oil-in-water emulsion. The active ingredigents for use herein will therefore have a solubility parameter from about 7 to about 13.

These emulsions are typically used with water to cleanse the skin. Upon rinsing with water, these compositions are removed from the skin surface along with associated dirt, oils, bacteria, and other foreign material, and leave the active ingredients deposited upon the skin.

The oil-in-water emulsions herein have desirable aesthetic properties, such as a rich and creamy, yet non-greasy, skin feel. These emulsions can span a broad range of consistencies from thin lotions to heavy creams. These emulsions typically have viscosities ranging from about 100 cps to about 500,000 cps, more preferably from about 1000 cps to about 150,000 cps, and most preferably from about 5000 cps to about 100,000 cps.

The emulsion compositions herein can span a wide range of pH values and can be acidic, basic, or neutral, depending on the particular active or actives employed. For example, for acidic actives, the pH of the composition should be carefully chosen so that it is at or below the pKa of the active. By standard definitions, the pKa value for a compound is that pH value at which the material is 50 percent dissociated or ionized to yield its conjugate base and a proton (or hydrated proton). Without being limited by theory, when the pH of the formulation is below the pKa of the active, it is belived that the active will exist primarily in its un-ionized form which should enhance its subsequent deposition onto the skin.

For example, salicylic acid has a reported pKa of 2.97 at 190° C. in aqueous solution. Therefore, it would be useful to formulate salicylic acid containing compositions at or below a pH of about 2.97 in order to suppress ionization and maximize deposition from the emulsion. See *CRC Handbook of Chemistry and Physics,* 57th Edition, page D-150 (1976). For salicylic acid containing compositions the should be from about 2 to about 7, more preferably from about 2.5 to about 5, even more preferably from about 2.5 to about 4, and most preferably from about 2.5 to about 3.

Even though buffers can be utilized to help maintain the pH of the emulsion compositions, these are not required components, but are merely optional.

(a) Active Ingredients

The emulsion compositions of the present invention comprise a safe and effective amount of an active ingredient which is deposited upon the skin surface during the cleansing process. These emulsions can contain a mixture of two or more active ingredients.

By the term "safe and effective amount" as used herein, means an amount of an active high enough to modify the condition to be treated or to deliver the desired skin benefit, but low enough to avoid serious side effects at a reasonable benefit to risk ratio within the scope of sound medical judgement. What is a safe and effective amount of the active will vary with the specific active, the ability of the active to penetrate through the skin, the age, health condition, and skin condition of the user, and other like factors.

Typically, the actives of the present invention comprise from about 0.05% to about 20%, more preferably from about 0.1% to about 10%, and most preferably from about 1% to about 5%.

The actives useful herein have a solubility parameter from about 7 to about 13, preferably from about 7.5 to about 12.5, and more preferably from about 8 to about 12. Solubility parameters are well known to the formulation chemist of ordinary skill in the art and are routinely used as a guide for determining compabilities and solubilities of materials in the formulation process. Without being limited by theory, it is believed that in choosing actives with solubility parameters in the above designated ranges that the actives will tend to be hydrophobic, i.e. lipophilic and therefore more soluble in the oil phase of the oil-in-water emulsions herein. The lipohilic nature of the active ingredients should help to enhance deposition of the active onto the skin from an oil-in-water emulsion upon rinsing of the emulsion with water. Generally, the actives useful herein will have a solubility in water at 25° C. of less than about 1 gram per about 100 grams of water.

The solubility parameter of a chemical compound, $\delta$, is defined as the square root of the cohesive energy density for that compound. Typically, a solubility parameter for a compound is calculated from tabulated values of the additive group contributions for the heat of vaporization and molar volume of the components of that compound, using the following equation:

$$\delta = \left[ \frac{\sum_i E_i}{\sum_i m_i} \right]^{1/2}$$

wherein $\sum_i E_i$ = the sum of the heat of vaporization additive group controbutions $\sum_i m_i$ = the sum of the molar volume additive group contributions Standard tabulations of heat of vaporization and molar volume additive group contributions for a wide variety of atoms and groups of atoms are collected in Barton, A. F. M. *Handbook of Solubility Parameters,* CRC Press, Chapter 6, Table 3, pp. 64–66 (1985), which is incorporated by reference herein in its entirety. The above solubility parameter equation is described in Fedors, R. F., "A Method for Estimating Both the Solubility Parameters and Molar Volumes of Liquids", *Polymer Engineering and Science,* vol. 14, no. 2, pp. 147–154 (February 1974), which is incoporated by reference herein in its entirety.

Calculated solubility parameters obey the law of mixtures such that the calculated solubility parameter for a mixture of materials is given by the weighted average of the calculated solubility parameters for each component of that mixture. See, *Handbook of Chemistry and Physics,* 57th edition, CRC Press, p. C-726 (1976–1977), which is incorporated by reference herein in its entirety.

Formulation chemists typically report and use solubility parameters in units of $(cal/cm^3)^{1/2}$. The tabulated values of additive group contributions for heat of vaporization in the *Handbook of Solubility Parameters* are reported in units of kJ/mol. However, these tabulated heat of vaporization values are readily converted to cal/mol using the following well-known relationships:

1 J/mol=0.239006 cal/mol and 1000J=1 kJ.

See Gordon, A. J. et al., *The Chemist's Companion,* John Wiley & Sons, pp. 456–463, (1972), which is incorporated by reference herein in its entirety.

Solubility parameters have also been tabulated for a wide variety of chemical compounds. Tabulations of solubility parameters are found in the *Handbook of Solubility Parameters.*

The actives useful herein can be categorized by their therapeutic benefit or their postulated mode of action. However, it is to be understood that the actives useful herein can in some instances provide more that one therapeutic benefit or operate via more than one mode of action. Therefore, any classifications herein are made for the sake of convenience and are not intended to limit the active to that particular application or applications listed. Among the classes of actives useful herein based on therapeutic benefit or mode of action are the following.

Anti-acne actives: Examples of useful anti-acne actives include the keratolytics such as salicylic acid, and resorcinol; retinoids such as retinoic acid and its derivatives (e.g., cis and trans); antibiotics and antimicrobials such as benzoyl peroxide, octopirox, erythromycin and its metal complexes (e.g., zinc erythromycin), tetracyclin, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavinoids; alpha and beta hydroxy acids; and bile salts such as scymnol sulfate and its derivatives, deoxycholate, and cholate.

Anti-wrinkle and anti-skin atropy actives: Examples of antiwrinkle and anti-skin atrophy actives include retinoic acid, salicylic acid, and skin peel agents (e.g., phenol and the like).

Non-steroidal anti-inflammatory actives (NSAIDS): Examples of NSAIDS include the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Examples of useful NSAIDS include acetyl salicylic acid, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Topical anesthetics: Examples of topical anesthetic drugs include lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Antimicrobial and antifungal actives: Examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate and clotrimazole.

Sunscreening actives: A wide variety of sunscreening actives are useful herein, and include those described in U.S. Pat. No. 5,087,445, to Haffey et al., issued Feb. 11, 1992; U.S. Pat. No. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*, all of which are incorporated herein by reference in their entirety. Nonlimiting examples of sunscreen actives include those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene)camphor, and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. These sunscreening agents provide higher efficacy, broader UV absorption, lower skin penetration and longer lasting efficacy relative to conventional sunscreens. Especially preferred examples of these sunscreens include those selected from the group consisting of 4-N,N-(2-ethylhexyl)methylaminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl) methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof.

Preferred examples of actives useful herein include those selected from the group consisting of salicylic acid, 3-hydroxy benzoic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, azelaic acid, arachidonic acid, benzoylperoxide, tetracyclin, ibuprofen, naproxen, hydrocortisone, acetominophen, erythromycin, zinc erythromycin, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, neocycin sulfate, 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene)camphor, 4-N,N-(2-ethylhexyl) methylaminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl) methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof.

More preferred examples of actives useful herein include those selected from the group consisting of salicylic acid, acetyl salicylic acid, cis-retinoic acid, trans-retinoic acid, azelaic acid, tetracyclin, ibuprofen, naproxen, acetominophen, hydrocortisone, erythromycin, zinc erythromycin, resorcinol, phenoxyethanol, phenoxypropanol, phenoxyisopropanol, 2,4,4'-trichloro-2'-hydroxy diphenyl ether, 3,4,4'-trichlorocarbanilide, octopirox, 2-ethylhexyl p-methoxycinnamate, 2-ethylhexyl N,N-dimethyl-p-aminobenzoate, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene)camphor, 4-N,N-(2-ethylhexyl)-methylaminobenzoic acid ester of 4-(2-hydroxyethoxy)dibenzoylmethane, and mixtures thereof.

Most preferred examples of actives useful herein include those selected from the group consisting of salicylic acid, cis-retinoic acid, trans-retinoic acid, azelaic acid, erythromycin, resorcinol, ibuprofen, naproxen, hydrocortisone, phenoxyethanol, phenoxypropanol, phenoxyisopropanol, 2,4,4'-trichloro-2'-hydroxy diphenyl ether, 3,4,4'-trichlorocarbanilide, 2-ethylhexyl p-methoxycinnamate, 2-ethylhexyl N,N-dimethyl-p-aminobenzoate, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene)camphor, 4-N,N-(2-ethylhexyl)-methylaminobenzoic acid ester of 4-(2-hydroxyethoxy) dibenzoylmethane, and mixtures thereof.

An especially preferred active useful herein is saliylic acid.

(b) Alkoxylated Ethers and Diethers

The compositions of the present invention comprise from about 0.1% to about 25%, preferably from about 0.1% to about 15%, and more preferably from about 6% to about 10% of an alkoxyalated ether which is useful for solubilizing the active ingredients in the oil phase of the oil-in-water emulsions. The alkoxylated ethers and diethers useful herein generally have a solubility in water of less than about 1 gram per about 100 grams of water at 25° C. These compounds are typically formulated into the oil phase of the oil-in-water emulsions as described in the Examples below. Mixtures of alkoxylated ethers and diethers can be used herein.

The alkoxylated ethers useful herein can be described by the following general formula:

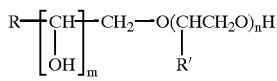

wherein R is selected from the group consisting of H and C1–C30 straight chain or branched chain alkyl, m is an integer from 0 to about 6, R' is selected from the group consisting of methyl and ethyl, and n is an integer from about 3 to about 30.

Preferably R is selected from the group consisting of C2–C25 straight chain or branched alkyl, m is an integer from 0 to about 2, R' is methyl, and n is an integer from about 5 to about 25. More preferably R is selected from the group consisting of C2–C20 straight chain or branched chain alkyl, m is an integer from 0 to about 1, R' is methyl, and n is an integer from about 10 to about 20.

Nonlimiting examples of classes of alkoxylated ethers useful herein include propoxylated and butoxylated ethers of alcohols and polyols. These compounds can be described as PPG and PBG alkyl ethers wherein the PPG and PBG are commonly used designations for polypropylene glycol and polybutylene glycol, respectively. The average number of PPG or PBG groups in these ethers is commonly given by a number designation after the PPG or PBG. For example, PPG-14 butyl ether, would designate a polypropylene glycol ether of butanol wherein the molecule has on average 14 propylene glycol units.

Nonlimiting examples of alkoxylated ethers useful herein include PPG-10 butyl ether, PPG-11 butyl ether, PPG-12 butyl ether, PPG-13 butyl ether, PPG-14 butyl ether, PPG-15 butyl ether, PPG-16 butyl ether, PPG-17 butyl ether, PPG-18 butyl ether, PPG-19 butyl ether, PPG-20 butyl ether, PPG-22 butyl ether, PPG-24 butyl ether, PPG-30 butyl ether, PPG-11 stearyl ether, PPG-15 stearyl ether, PPG-10 oleyl ether, PPG-7 lauryl ether, PPG-30 isocetyl ether, PPG-10 glyceryl ether, PPG-15 glyceryl ether, PPG-10 butyleneglycol ether, PPG-15 butylene glycol ether, PPG-27 glyceryl ether, PPG-30 cetyl ether, PPG-28 cetyl ether, PPG-10 cetyl ether, PPG-10 hexylene glycol ether, PPG-15 hexylene glycol ether, PPG-10 1,2,6-hexanetriol ether, PPG-15 1,2,6-hexanetriol ether, and mixtures thereof.

Preferred alkoxylated ethers are those selected from the group consisting of PPG-14 butyl ether, PPG-15 stearyl ether, PPG-11 stearyl ether, PPG-20 oleyl ether, and mixtures thereof.

More preferred alkoxylated ethers are those selected from the group consisting of PPG-14 butyl ether, PPG-15 stearyl ether, and mixtures thereof. PPG-14 butyl ether is available under the tradename Fluid AP from Union Carbide Corporation. PPG 15 stearyl ether is available under the tradename Arlamol E from ICI Americas Corporation.

Also useful herein are alkoxylated diethers. These compounds can be represented by the general formula:

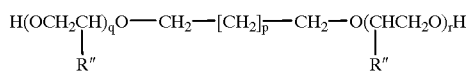

wherein each R" is selected from the group consisting of methyl and ethyl, p is an integer from about 1 to about 6, and each q and r are independently selected so that their sum is an integer from about 3 to about 30. Preferably R" is methyl, p is an integer from about 2 to about 4, and each q and r are independently selected so that their sum is an integer from about 5 to about 25. More preferably R" is methyl, p is an integer from 2 to about 4, and each q and r are independently selected so that their sum is an integer from about 10 to about 20.

Nonlimiting examples of alkoxylated diethers useful herein include those selected from the group consisting of PPG-10 1,4-butanediol diether, PPG-12 1,4-butanediol diether, PPG-14 1,4-butanediol diether, PPG-2 butanediol diether, PPG-10 1,6-hexanediol diether, PPG-12 1,6-hexanediol diether, PPG-14 hexanediol diether, PPG-20 hexanediol diether, and mixtures thereof. Preferred are those selected from the group consisting of PPG-10 1,4-butanediol diether, PPG-12 1,4-butanediol diether, PPG-10 1,6-hexandiol diether, and PPG-12 hexanediol diether, and mixtures thereof. More preferred is PPG-10 1,4-butanediol diether. This compound is commercially available under the tradename Macol 57 from PPG/Mazer Corporation.

(c) Emulsifier

The compositions of the present invention comprise from about 0.1% to about 10%, preferably from about 0.2% to about 5%, and more preferably from about 0.25% to about 2.5% of at least one emulsifier. The emulsifier is used herein for emulsifying the oil and water phase ingredients and for stabilizing the resulting emulsion. Even though the term "emulsifier" is used herein to describe these materials, this term is not intended to exclude those emulsifiers which also have surfactant properties.

The emulsifiers useful herein can include any of a wide variety of nonionic, cationic, anionic, and zwitterionic emulsifiers disclosed in prior patents and other references. See McCutcheon's, *Detergents and Emulsifiers*, North American Edition (1986), published by Allured Publishing Corporation; U.S. Pat. No. No. 5,011,681 to Ciotti et al., issued Apr. 30, 1991; U.S. Pat. No. No. 4,421,769 to Dixon et al., issued Dec. 20, 1983; and U.S. Pat. No. 3,755,560 to Dickert et al., issued August 28, 1973; these four references are incorporated herein by reference in their entirety.

The exact emulsifier chosen will depend upon the pH of the composition and the other components present. Suitable emulsifier types include tetra-alkyl ammonium salts, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Preferred herein, especially when the emulsions have a pH from about 2 to about 7, are cationic emulsifiers. A wide variety of cationic emulsifiers and surfactants useful herein are disclosed in U.S. Pat. No. 5,151,209, to McCall et al., issued Sep. 29, 1992; U.S. Pat. No. 5,151,210, to Steuri et al., issued Sep. 29, 1992; U.S. Pat. No. 5,120,532, to Wells et al., issued Jun. 9, 1992; U.S. Pat. No. 4,387,090, to Bolich, issued Jun. 7, 1983;; U.S. Pat. No. 3,155,591, Hilfer, issued Nov. 3, 1964; U.S. Pat. No. 3,929,678, to Laughlin et al., issued Dec. 30, 1975; U.S. Pat. No. 3,959,461, to Bailey et al., issued May 25, 1976; *McCutcheon's, Detergents & Emulsifiers*, (North American edition 1979) M.C. Publishing Co.; and Schwartz, et al., *Surface Active Agents, Their Chemistry and Technology*, New York: Interscience Publishers, 1949; all of these documents being incorporated herein by reference in their entirety.

The cationic emulsifiers useful herein include cationic ammonium salts such as those having the formula:

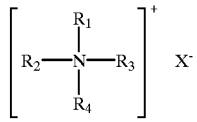

wherein $R_1$, is selected from an alkyl group having from about 12 to about 22 carbon atoms, or aromatic, aryl or alkaryl groups having from about 12 to about 22 carbon atoms; $R_2$, $R_3$, and $R_4$ are independently selected from hydrogen, an alkyl group having from about 1 to about 22 carbon atoms, or aromatic, aryl or alkaryl groups having from about 12 to about 22 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties).

More preferably, $R_1$ is an alkyl group having from about 12 to about 22 carbon atoms; $R_2$ is selected from H or an alkyl group having from about 1 to about 22 carbon atoms; $R_3$ and $R_4$ are independently selected from H or an alkyl group having from about 1 to about 3 carbon atoms; and X is as described in the previous paragraph.

Most preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Alternatively, other useful cationic emulsifiers include amino-amides, wherein in the above structure $R_1$ is alternatively $R_5CO-(CH_2)_n-$, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic emulsifiers include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a cocunt fatty acid, which generally have mixtures of alkyl chains in the C12 to C14 range. Examples of quaternary ammonium salts derived from these tallow and cococut sources include ditallow dimethyl ammonium chlroide, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

More preferred cationic emulsifiers are those selected from the group consisting of dilauryl dimethyl ammoniun chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Most preferred cationic emulsifiers are those selected from the group consisting of dilauryl dimethyl ammoniun chloride, distearyl dimethyl ammonium chloride, dimyristyl dimethyl ammonium chloride, dipalmityl dimethyl ammonium chloride, distearyl dimethyl ammonium chloride, and mixtures thereof.

Also, preferred for use herein are certain nonionic emulsifiers, especially when used in combination with the cationic emulsifiers described above. It has been found that a blend of a high HLB nonionic emulsifier with a low HLB nonionic emulsifer is especially preferred. Without being limited by theory, it is believed that this combination of both high and low HLB nonionic emulsifiers provides compositions demonstrating enhnaced emulsion stability. The abbreviation "HLB" stands for hydrophilic lipophilic balance. The HLB system is well known in the art and is described in detail in "The HLB System, A Time-Saving Guide to Emulsifier Selection", ICI Americas Inc., August 1984, which is incorporated herein by reference.

As defined herein the high HLB nonionic emulsifiers include any of the well-known nonionic emulsifiers that have an HLB of from about 6 to about 18, preferably from about 8 to about 18, and more preferably from about 10 to about 18. These high HLB nonionic emulsifiers do not include those emulsifiers with HLB values less than 6, as described below. Typical of these high HLB nonionic emulsifiers are ethoxylated or propoxylated, preferably ethoxylated, alcohols and alkyl phenols, with the alcohol derivatives being preferred. In general, these alcohol derivatives contain a straight or branched chain alkyl group in the $C_{8-22}$, preferably $C_{10-20}$, more preferably $C_{12-20}$, range and generally contain from about 6 to about 30, preferably from about 6 to about 25, ethylene oxide or propylene oxide groups. Among these ethoxylated and propoxylated alcohols, the ethoxylated derivatives are most preferred. Preferred for use herein are polyethylene oxide ethers derived from lauryl alcohol, cetyl alcohol, oleyl alcohol, stearyl alcohol, isostearyl alcohol, myristyl alcohol, behenyl alcohol, and mixtures thereof. More preferred for use herein are: polyoxyethylene 10 cetyl ether, known by the CTFA designation as ceteth-10; polyoxyethylene (21) stearyl ether, known by the CTFA designation steareth-21; coconut alkyl polyethoxylate (6.5); decyl polyethoxylate (6); and mixtures thereof. Most preferred for use herein are ceteth-10, steareth-21, and mixtures thereof.

Detailed listings of high HLB nonionic emulsifiers can be found in McCutcheon's EMULSIFIERS AND DETERGENTS, North American Edition, 1984, McCutcheon Division, MC Publishing Company, which has already been incorporated herein by reference.

The low HLB nonionic emulsifiers are defined herein as any of the well known nonionic emulsifiers having an HLB value from about 1 to about, but not greater than or equal to, 6. These low HLB nonionic emulsifiers do not include the high HLB nonionic emulsifer described above.

Examples of these low HLB nonionic emulsifiers are ethoxylated alcohols with the alcohol derivatives being preferred. In general, these alcohol derivatives contain a straight or branched chain alkyl group in the $C_{8-22}$, preferably $C_{10-20}$, more preferably $C_{12-20}$, range, and generally contain from about 1 to about 5 ethylene oxide groups per molecule.

Some nonlimiting examples of these low HLB nonionic emulsifiers useful herein include stearic acid ethoxylated with 1 mole of ethylene oxide (i.e. steareth-1), steareth-2, steareth-3, steareth-4, steareth-5, ceteth-1, cetheth-2, ceteth-3, ceteth-4, ceteth-5, laureth-1, laureth-2, laureth-3, laureth-4, laureth-5, and mixtures thereof. Preferred low HLB nonionic emulsifiers are steareth-1, steareth-2, steareth-3, ceteth-1, ceteth-2, cetheth-3, laureth-1, laureth-2, laureth-3, and mixtures thereof. More preferred are steareth-2, ceteth-2, laureth-2, and mixtures thereof. Most preferred is steareth-2, which is available commercially as Brij 72 from ICI Americas.

Detailed listings of low HLB emulsifiers can be found in McCutcheon's EMULSIFIERS AND DETERGENTS, North American Edition, 1984, McCutcheon Division, MC Publishing Company, which has already been incorporated herein by reference.

In the present invention, it has been found that when a combination of a high and a low HLB nonionic emulsifer are used together, that the combination of steareth-21 and/or ceteth-10 with steareth-2 is preferred.

(d) Deposition Aiding Polymer

The compositions of the present invention comprise from 0% to about 10%, preferably from about 0.1% to about 10%, more preferably from about 0.25% to about 7.5%, and most preferably from about 0.50% to about 5% of a deposition aiding polymer for increasing the deposition of the active ingredient upon the skin. Without being limited by theory, the deposition aiding polymer is believed to aid in the deposition of the active ingredient from the oil phase of the oil-in-water emulsion, thereby depositing the active onto the skin during the cleansing process and helping the active to adhere to the skin during the rinsing process. The deposition aiding polymers useful herein are typically formulated into the oil phase of the oil-in-water emulsions as described in the Examples below.

A variety of deposition aiding polymers are useful herein and include those selected from the group consisting of hydroxy-terminated urethane polymers, polypropylene glycols, and mixtures thereof.

When a combination of a hydroxy-terminated urethane polymer and a polypropylene glycol polymer is used as the deposition aiding polymer, the weight/weight ratio of the hydroxy-terminated urethane polymer to the polypropylene glycol polymer is from about 1:1.5 to about 1.5:1, preferably from about 1.25:1 to about 1:1.25, more preferably from about 1.1:1 to about 1:1.1, and most preferably about 1:1.

Hydroxy-terminated Urethane Polymers

The hydroxy-terminated urethane polymers useful as deposition aids herein are those generally described in U.S. Pat. No. 5,051,260, to Chess et al., issued Sep. 24, 1991; U.S. Pat. No. 5,045,317, to Chess et al. issued Sep. 3, 1991; and U.S. Pat. No. 4,971,800, to Chess et al., issued Nov. 20, 1990; all of which are incorporated by reference herein in their entirety.

These hydroxy-terminated urethane compounds are represented by the general formula (it is to be understood that this formula represents a linear polymer chain and is depicted as such merely for convenience and space constraints):

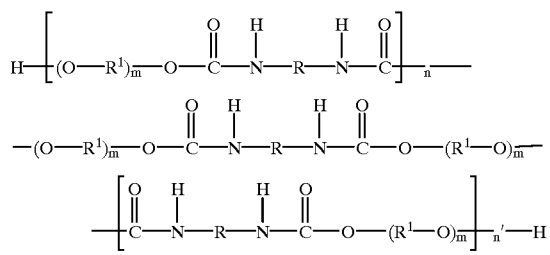

wherein R represents an alkyl or alkenyl radical having from about one to about 20 carbon atoms, or a cycloalkyl or cycloalkyneyl radical containing form about 5 to about 10 carbon atoms, or a mononuclear or fused ring aryl radical containing from about 6 to about 10 carbon atoms, unsubstituted or substituted with one or more C1–C6 alkyl, C1–C6 alkoxy, C1–C6 alkoxy-substituted C1–C6, nitro or amino groups or halogen atoms; $R^1$ is the same or different alkyl or akenyl radical; m is an integer selected so as to provide an ($O—R^1$) moiety having a molecular weight of from about 40 to about 6000, preferably from about 400 to about 2000; and n and n' are the same or different integers of from 0 to about 30 inclusive, correlated with m so as to provide a hydroxy-terminated urethane compound having a molecular weight of up to about 200,000, preferably from about 220 to about 37,000, and more preferably from about 1000 to about 5000.

The hydroxy-terminated urethane compounds are prepared using standard synthetic techniques from the reaction of linear alkylene or polyalkylene glycols or polyethers with monomeric organic diisocyanates. The linear alkylene or polyalkylene glycols or polyethers are represented by the general formula:

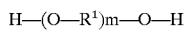

wherein $R^1$ and m are as described in the preceding paragraph. Specific nonlimiting examples of polyalkylene glycol or polyether reactants include: diethylene glycol, triethylene glycol, PEG-4, PEG-6, PEG-8, PEG-9, PEG-10, PEG-12, PEG-14, PEG-16, PEG-18, PEG-20, PEG-32, PEG-40, PPG-9, PPG-12, PPG-15, PPG-17, PPG-20, PPG-26, PPG-30, PPG-34, and polytetramethylene glycols having molecular weights ranging from about 600 to 6000, and the like. The terms "PEG" and "PPG" are commonly used CTFA designations for polyethylene glycol and polypropylene glycol, respectively. The number following the designation indicates the average number of units of ethylene glycol or propylene glycol in the molecule. Also, mixtures of polyalkylene glycols or polyethers described hereinabove can also be employed in preparing the hydroxy-terminated urethanes useful herein. The monomeric organic diisocyanates are represented by the general formula:

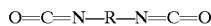

wherein R is an alkyl or alkenyl radical having from about one to about 20 carbon atoms, or a cycloalkyl or cycloalkyneyl radical containing form about 5 to about 10 carbon atoms, or a mononuclear or fused ring aryl radical containing from about 6 to about 10 carbon atoms, unsubstituted or substituted with one or more C1–C6 alkyl, C1–C6 alkoxy, C1–C6 alkoxy-substituted C1–C6, nitro or amino groups or halogen atoms. Nonlimiting examples of diisocyanates are aromatic diisocyanates, such as m-phenylenediisocyanate, p-phenylenediisocyanate, 4-t-butyl-m-phenylenediisocyanate, 4-methoxy-m-phenylenediisocyanate, 4-phenoxy-m-phenylenediisocyanate, 4-chloro-m-phenylenediisocyanate, toluenediisocyanates (either as a mixture of isomers, e.g., the commercially available mixture of 80% 2,4-toluenediisocyanate and 20% 2,6-toluenediisocyanate, or as the individual isomers themselves), m-xylylenediisocyanate, p-xylylendiisocyanate, cumene-2,4-diisocyanate, durenediisocyanate, 1,4-naphthylenediisocyanate, 1,5-naphthylenediisocyanate, 1,8-naphthylenediisocyanate, 2,6-naphthylenediisocyanate, 1,5-tetrahydronophthylenediisocyanate, p,p'-diphenyldiisocyanate, diphenylmethane-4,4'-diisocyanate, 2,4-diphenylhexane-1,6-diisocyanate, "bitolylenediisocyanate" (3,3'-dimethyl-4,4'-biphenylenediisocyanate), "dianisidinediisocyanate" (3,3'-dimethoxy-4,4'-biphenylenediisocyanate); aliphatic diisocyanates, such as methylenediisocyanates, ethylenediisocyanate, the tri-, tetra-, penta-, hexa-, octa-, nona- and decamethylene-omega, omega-diisocyanates, 2-chloro-trimethylenediisocyanate, 2,3-dimethyltetramethylenediisocyante, and the like, as well as mixtures thereof.

A preferred hydroxy-terminated urethane polymer useful herein is poly[oxy(methyl-1,2-ethanediyl)],alpha-hydro-omega-hydroxy-, polymer with 1,1'methylene-bis-(4-isocyanatocyclohexane). This material is also known by the CTFA designation polyolprepolymer-2 and is commercially available as Topicare 35A from Penederm Inc. through its distributor Barnet Products Corp. (Englewood Cliffs, N.J.).

Polypropylene Glycols

Polypropylene glycols are useful as deposition aiding polymers herein. Polypropylene glycols are polymers which are typically formed from the polymerization of propylene oxide, propylene glycol, propylchlorohydrin, propylbromohydrin, and other related materials. Polypropylene glycols are represented by the following formula.

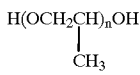

wherein n is an integer from about 10 to about 50, preferably wherein n is an integer from about 15 to about 40, and more preferably wherein n is an integer from about 20 to about 34. In the above structure, even though one isomeric orientation is depicted for convenience, this depiction is not intended to preclude other isomeric structures. The polypropylene glycols are commonly desiginated as PPG's followed by a number indicating the average number of repeating units in the structure. For example, PPG-30 would correspond to the above structure wherein n has an average value of about 30. Based on this nomenclature, the polypropylene glycols useful herein encompass those designated as PPG-10 through PPG-50, more preferably those designated as PPG-15 through PPG-40, and most preferably those designated as PPG-20 through PPG-34. An especially preferred PPG for use in the compositions herein is PPG-30, which is sold under the tradename Polyglycol P-4000 and is commercially available from Dow Chemical Corporation.

(e) Polymeric Thickener

The compositions of the present invention comprise from 0% to about 10%, preferably from about 0.5% to about 5%, and more preferably from about 1% to about 4% of a polymeric thickener. A wide variety of thickeners can be employed herein with the choice depending upon the pH of the formulation and other emulsion components chosen. For compositions having a pH from about 2 to about 7, the thickeners should be stable within that pH range, i.e. they should not degrade and should not lose their thickening ability.

Preferred thickeners include those selected from the group consisting of crosslinked polyacrylate polymers, alkyl modified hydroxyalkylcellulose polymers, quaternary ammonium hydroxalkyl celluose polymers, and mixtures thereof.

Crosslinked Polyacrylate Polymers

The crosslinked polyacrylate polymers useful as thickeners include both cationic and nonionic polymers, with the cationics being generally preferred.

Examples of useful crosslinked nonionic polyacrylate polymers and crosslinked cationic polyacrylate polymers are those described in U.S. Pat. No. 5,100,660, to Hawe et al., issued Mar. 31, 1992; U.S. Pat. No. 4,849,484, to Heard, issued Jul. 18, 1989; U.S. Pat. No. 4,835,206, to Farrar et al., issued May 30, 1989; U.S. Pat. No. 4,628,078 to Glover et al. issued Dec. 9, 1986; U.S. Pat. No. 4,599,379 to Flesher et al. issued Jul. 8, 1986; and EP 228,868, to Farrar et al., published Jul. 15, 1987; all of which are incorporated by reference herein in their entirety.

The crosslinked polyacrylate polymers are high molecular weight materials that can be characterized by the general formula: $(A)_l(B)_m(C)_n$ and comprise the monomer units $(A)_l$, $(B)_m$, and $(C)_n$, wherein (A) is a dialkylaminoalkyl acrylate monomer or its quaternary ammonium or acid addition salt, (B) is a dialkylaminoalkyl methacrylate monomer or its quaternary ammonium or acid addition salt, (C) is a monomer that is polymerizable with (A) or (B), for example a monomer having a carbon-carbon double bond or other such polymerizable functional group, l is an integer of 0 or greater, m is an integer of 0 or greater, n is an integer of 0 or greater, but where either l or m, or both, must be 1 or greater.

The (C) monomer can be selected from any of the commonly used monomers. Nonlimiting examples of these monomers include ethylene, propylene, butylene, isobutylene, eicosene, maleic anhydride, acrylamide, methacrylamide, maleic acid, acrolein, cyclohexene, ethyl vinyl ether, and methyl vinyl ether. In the cationic polymers of the present invention, (C) is preferably acrylamide. The alkyl portions of the (A) and (B) monomers are short chain length alkyls such as $C_1$–$C_8$, preferably $C_1$–$C_5$, more preferably $C_1$–$C_3$, and most preferably $C_1$–$C_2$. When quaternzied, the polymers are preferably quaternized with short chain alkyls, i.e., $C_1$–$C_8$, preferably $C_1$–$C_5$, more preferably $C_1$–$C_3$, and most preferably $C_1$–$C_2$. The acid addition salts refer to polymers having protonated amino groups. Acid addition salts can be performed through the use of halogen (e.g. chloride), acetic, phosphoric, nitric, citric, or other acids.

These $(A)_l(B)_m(C)_n$ polymers also comprise a crosslinking agent, which is most typically a material containing two or more unsaturated functional groups. The crosslinking agent is reacted with the monomer units of the polymer and is incorporated into the polymer thereby forming links or covalent bonds between two or more individual polymer chains or between two or more sections of the same polymer chain. Nonlimiting examples of suitable crosslinking agents include those selected from the group consisting of methylenebisacrylamides, diallyldialkyl ammonium halides, polyalkenyl polyethers of polyhydric alcohols, allyl acrylates, vinyloxyalkylacrylates, and polyfunctional vinylidenes. Specific examples of crosslinking agents useful herein include those selected from the group consisting of methylenebisacrylamide, ethylene glycol di-(meth)acrylate, di-(meth)acrylamide, cyanomethylacrylate, vinyloxyethylacrylate, vinyloxyethylmethacrylate, allyl pentaerythritol, trimethylolpropane diallylether, allyl sucrose, butadiene, isoprene, divinyl benzene, divinyl naphthalene, ethyl vinyl ether, methyl vinyl ether, and allyl acrylate. Other crosslinkers include formaldehyde and glyoxal. Preferred for use herein as a crosslinking agent is methylenebisacrylamide.

Widely varying amounts of the crosslinking agent can be employed depending upon the properties desired in the final polymer, e.g. viscosifying effect. Without being limited by theory, it is believed that incorporation of a crosslinking agent into these cationic polymers provides a material that is a more effective viscosifying agent without negatives such as stringiness and viscosity breakdown in the presence of electrolytes. The crosslinking agent, when present, can comprise from about 1 ppm to about 1000 ppm, preferably from about 5 ppm to about 750 ppm, more preferably from about 25 ppm to about 500 ppm, even more preferably from about 100 ppm to about 500 ppm, and most preferably from about 250 ppm to about about 500 ppm of the total weight of the polymer on a weight/weight basis.

The intrinsic viscosity of the crosslinked polymer, measured in one molar sodium chloride solution at 25° C., is generally above 6, preferably from about 8 to about 14. The molecular weight (weight average) of the crosslinked polymers hereof is high, and is believed to typically be between about 1 million and about 30 million. The specific molecular weight is not critical and lower or higher weight average molecular weights can be used as long as the polymer retains its intended viscosifying effects in water or other aqueous carriers of the compositions hereof. Preferably, a 1.0% solution of the polymer (on an actives basis) in deionized water will have a viscosity at 25° C. of at least about 20,000 cP, preferably at least about 30,000 cP, when measured at 20 RPM by a Brookfield RVT (Brookfield Engineering Laboratories, Inc. Stoughton, Mass., USA).

These cationic polymers can be made by polymerization of an aqueous solution containing from about 20% to about 60%, generally from about 25% to about 40%, by weight monomer, in the presence of an initiator (usually redox or thermal) until the polymerization terminates. The crosslinking agent can also be added to the solution of the monomers to be polymerized, to incorporate it into the polymer. In the polymerization reactions, the temperature generally starts between about 0° and 95° C. The polymerization can be conducted by forming a reverse phase dispersion of an aqueous phase of the monomers (and also any additional crosslinking agents) into a nonaqueous liquid, e.g. mineral oil, lanolin, isododecane, oleyl alcohol, and other volatile and nonvolatile esters, ethers, and alcohols, and the like.

All percentages describing the polymer in this section of the description herein are molar, unless otherwise specified.

When the polymer contains (C) monomer, the molar proportion of (C) monomer, based on the total molar amount of (A), (B), and (C), can be from 0% to about 99%. The molar proportions of (A) and (B) can each be from 0% to 100%. When acrylamide, is used as the (C) monomer, it will preferably be used at a level of from about 20% to about 99%, more preferably from about 50% to about 90%.

Where monomer (A) and (B) are both present, the ratio of monomer (A) to monomer (B) in the final polymer, on a molar basis, is preferably from about 99:5 to about 15:85, more preferably from about 80:20 to about 20:80.

Alternatively, in another class of polymers, the ratio is from about 5:95 to about 50:50, preferably from about 5:95 to about 25:75.

In another alternative class of polymers, the ratio (A):(B) is from about 50:50 to about 85:15. Preferably the ratio (A):(B) is about 60:40 to about 85:15, most preferably about 75:25 to about 85:15.

Most preferred is where monomer (A) is not present and the ratio of monomer (B):monomer (C) is from about 30:70 to about 70:30, preferably from about 40:60 to about 60:40 and most preferably from about 45:55 to about 55:45.

Cationic polymers that are useful herein that are especially preferred are those conforming to the general structure $(A)_l(B)_m(C)_n$ wherein l is zero, (B) is methyl quaternized dimethylaminoethyl methacrylate, the ratio of (B):(C) is from about 45:55 to about 55:45, and the crosslinking agent is methylenebisacrylamide. An example of such a cationic polymer is one that is commercially available as a mineral oil dispersion (which can also include various dispersing aids such as PPG-1 trideceth-6) under the trademark Salcare$^R$ SC92 from Allied Colloids Ltd. (Norfolk, Va.). This polymer has the proposed CTFA designation, "Polyquaternium 32 (and) Mineral Oil".

Other cationic polymers useful herein, are those not containing acrylamide or other (C) monomers, that is, n is zero. In these polymers the (A) and (B) monomer components are as described above. An especially preferred group of these non-acrylamide containing polymers is one in which l is also zero. In this instance the polymer is essentially a homopolymer of a dialkylaminoalkyl methacrlyate monomer or its quaternary ammonium or acid addition salt. These diaklylaminoalkyl methacrylate polymers preferably contain a crosslinking agent as described above.

A cationic polymer, which is essentially a homopolymer, useful herein is one conforming to the general structure $(A)_l(B)_m(C)_n$ wherein l is zero, (B) is methyl quaternized dimethylaminoethyl methacrylate, n is zero, and the crosslinking agent is methylenebisacrylamide. An example of such a homopolymer is commercially available as a mixture containing approximately 50% of the polymer, approximately 44% mineral oil, and approximately 6% PPG-1 trideceth-6 as a dispersing aid, from Allied Colloids Ltd, (Norfolk, Va.) under the trademark Salcare$^R$ SC95. This polymer has recently been given the CTFA designation "Polyquaternium 37 (and) Mineral Oil (and) PPG-1 Trideceth-6".

Alkyl Hydroxyalkylcellulose Ethers

By the term "alkyl hydroxyalkylcellulose ethers" as used herein is meant polymers containing a cellulose backbone, i.e. a polysaccharaide backobone of repeating glucose units. In these polymers, the hydroxy groups of the cellulose polymer are hydroyxalkylated (prefereably hydroxyethylated or hydropropylated) to form a hydroxyalkylated cellulose which is then further modified with a C10–C30 straight chain or branched chain alkyl group through an ether linkage. Typically these polymers are ethers of C10–C30 straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, rincioleyl, behenyl,and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol CS Plus from Aqualon Corporation.

Quaternary Ammonium Hydroxyalkylcellulose Polymers

By the term "quaternary ammonium hydroyxalkylcellulose polymer" as used herein is meant polymers containing a cellulose backbone, i.e. a polysaccharaide backobone of repeating glucose units. In these polymers, the hydroxy groups of the cellulose polymer are hydroxyalkylated (preferably hydroxyethylated or hydroxypropylated) to form a hydroxyalkylated cellulose which is then further modified with a cationic quaternary ammonium or protonated ammonium group.

Preferred cationic modifying groups are those having at least one C10–20 alkyl chain and two shorter alkyl chains (i.e. C1 or C2) on the nitrogen. The substituent on the cellulose polymer can thus be depicted as —(X)NRR'R" wherein X is hydroxyalkyl (preferably —OCH$_2$CH$_2$— or —OCH$_2$CHOHCH$_2$—), R and R' are methyl or ethyl, and R" is C10–20 alkyl [preferably lauryl, stearyl, or cocoyl (i.e. a mixture of alkyl groups derived from coconut oil)]. It has alternatively been found that when R, R', and R" are all methyl (i.e. the trimonium group) that useful cellulose polymers are also obtained.

In other alternatives structures, the substituent on the cellulose polymer can be depicted as —(X)—OCH$_2$CH$_2$—NRR'R" wherein X is hydroxyalkyl (preferably —OCH$_2$CH$_2$— or —OCH$_2$CHOHCH$_2$—), R and R' are methyl or ethyl, and R" is C10–20 alkyl [preferably lauryl, stearyl, or cocoyl (i.e. a mixture of alkyl groups derived from coconut oil)]. It has alternatively been found that when R, R', and R" are all methyl (i.e. the trimonium group) that useful cellulose polymers are also obtained.

In yet other alternative structures the cationic substituent on the cellulose contains both a hydroxyethyl and a hydroxypropyl group such that the moiety can be depicted as —(OCH$_2$CH$_2$O)—CH$_2$CHOHCH$_2$NRR'R" wherein R, R', and R" are methyl or ethyl, and R" is C10 –20 alkyl [preferably lauryl, stearyl, or cocoyl (i.e. a mixture of alkyl groups derived from coconut oil)], or alternatively wherein R, R', and R" are all methyl (i.e. the trimonium group).

Commercially available cationic modified celluloses include: CTFA designated polyquaternium-24, which is the quaternary ammonium salt of hydroxyethyl cellulose reacted with a lauryl dimethyl ammonium substituted epoxide (wherein in the above formula —(X)— OCH$_2$CH$_2$—NRR'R", X is —OCH$_2$CH$_2$—, R and R' are methyl, and R" is stearyl). This material is sold under the tradename Quatrisoft Polymer LM-200 and is available from Amerchol Corporation.

Other commericially available cationic modified celluloses inlcude: laurdimonium hydroxethyl cellulose (wherein in the above formula —(X)NRR'R", X is —OCH$_2$CH$_2$—, R and R' are methyl, and R" is lauryl), steardimonium hydroxyethyl cellulose (wherein in the above formula —(X)NRR'R", X is —OCH$_2$CH$_2$—, R and R' are methyl, and R" is stearyl), and cocodimonium hydroxyethyl cellulose (wherein in the above formula —(X)NRR'R", X is —OCH$_2$CH$_2$—, R and R' are methyl, and R" is cocoyl). These three materials are known by the trade names Crodacel QL, Crodacel QS, and Crodacel QM, respectively, which are all commercially available from Croda Corp. Another highly useful cationic cellulose is laurdimmonium hydroxypropyl oxyethyl cellulose (wherein the modifying group on the cellulose is —(OCH$_2$CH$_2$O)— CH$_2$CHOHCH$_2$NRR'R", wherein R R' are methyl and R" is lauryl), which is commercially available as Crodacel QL Special, from Croda Corp. p Preferred among the quaternary ammonium hydroalkyl cellulose polymers is polyquaternium-24.

(f) Water

The emulsions of the present invention comprise from about 25% to about 99.7%, more preferably from about 65% to about 95%, and most preferably from about 70% to about 90% water.

Optional Components

Each of the water and oil phases of the emulsions can comprise a wide variety of optional components. Typical of such optional components are:

Fatty Acids

An optional component of the present invention is a fatty acid. These fatty acids can be used to increase emulsion viscosity and to provide a smooth feel to the finished emulsion. When used herein, these fatty acids can comprise from about 0.1% to about 10%, more preferably from about 0.1% to about 7.5%, and most preferably from about 0.1% to about 5% of the compositions.

By the term "fatty acid" is meant any organic acid from natural or synthetic sources having from about 10 to about 40 carbon atoms, more preferably from about 10 to about 30 carbon atoms, and most preferably from about 12 to about 22 carbon atoms. Also included within this definition of fatty acid are the corresponding branched carbon chain materials.

Nonlimiting examples of fatty alcohols include those selected from the group consisting of lauric acid, myristic acid, palmitic acid, stearic acid, isostearic acid, oleic acid, linoleic acid, linolenic acid, ricinoleic acid, behenic acid, isostearic acid, and mixtures thereof. Examples of fatty alcohols are described in *CTFA International Cosmetic Ingredient Dictionary* Fourth Edition, which is incorporated herein by reference in its entirety.

Also useful are hydroxy substituted derivatives of the fatty acids described herein. Nonlimiting examples of these materials include hydroxystearic acid, hydroxypalmitic acid, hydroxylauric acid, and mixtures thereof.

Fatty Alcohol

An optional component of the present invention is a fatty alcohol. These fatty alochols can be used to increase emulsion viscosity and to provide a smooth feel to the finished emulsion. When used herein, these fatty alcohols can comprise from about 0.1% to about 10%, more preferably from about 0.1% to about 7.5%, and most preferably from about 0.1% to about 5% of the compositions.

By the term "fatty alcohol" is meant any organic alcohol from natural or synthetic sources having from about 10 to about 40 carbon atoms, more preferably from about 10 to about 30 carbon atoms, and most preferably from about 12 to about 22 carbon atoms. Also included within this definition of fatty alcohol are the corresponding branched carbon chain materials.

Nonlimiting examples of fatty alcohols include those selected from the group consisting of lauryl alcohol, myristyl alcohol, cetyl alcohol, stearyl alcohol, isostearyl alcohol, oleyl alcohol, linoleyl alcohol, linolenyl alcohol, ricinoleyl alcohol, behenyl alcohol, and mixtures thereof. Examples of fatty alcohols are described in *CTFA International Cosmetic Ingredient Dictionary* Fourth Edition, which is incorporated herein by reference in its entirety.

Humectants

Another optional component of the compositions of the present invention is a humectant. When used herein, the humectant can comprise from about 0.1% to about 20%, more preferably from about 0.5% to about 10%, and most preferably from about 1% to about 5% of the compositions. Even though these materials are defined herein as humectants, they can also possess moisturizing, skin conditioning, and other related properties.

Examples of humectants useful herein include materials such as urea; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, low molecular weight polypropylene glycols (e.g., dipropylene glycol and tripropylene glycol), hexanetriol, propylene glycol, butylene glycol, hexylene glycol, and the like; polyethylene glycol; sugars and starches; sugar and starch derivatives (e.g., alkoxylated glucose); hyaluronic acid; chitin, starch-grafted sodium polyacrylates such as Sanwet (RTM) IM-1000, IM-1500, and IM-2500 (available from Celanese Superabsorbent Materials, Portsmouth, Va.); lactamide monoethanolamine; acetamide monoethanolamine; propoxylated glycerol (as described in U.S. Pat. No. 4,976,953 to Orr et al., issued Dec. 11, 1990, which is incorporated by reference herein in its entirety); and mixtures thereof.

Preferred humectants useful in the compositions of the present invention are urea, C3–C6 diols and triols, low molecular weight polypropylene glycols, and propoxylated glycerin. Preferred humectants include those materials selected from the group consisting of urea, propylene glycol, 1,3-dihydroxypropane, glycerin, butylene glycol, hexylene glycol, 1,4-dihydroxyhexane, 1,2,6-hexanetriol, dipropylene glycol, tripropylene glycol, and mixtures thereof. More preferred are those selected from the group consisting of urea, glycerin, butylene glycol, hexylene glycol, glycerin, dipropylene glycol, tripropylene glycol, and mixtures thereof. Most preferred is urea, glycerin, and mixtures thereof.

Emollients

The compositions of the present invention can also include an emollient. Examples of suitable emollients include, but are not limited to, volatile and non-volatile silicone oils (e.g., dimethicone, cyclomethicone, dimethiconol, and the like), highly branched hydrocarbons, and non-polar carboxylic acid and alcohol esters, and mixtures thereof. Emollients useful in the instant invention are further described in U.S. Pat. No. 4,919,934, to Deckner et al., issued Apr. 24 1990, which is incorporated herein by reference in its entirety.

The emollients can typically comprise in total from about 0.5% to about 50%, more preferably from about 0.5% to about 25%, and most preferably from about 0.5% to about 15% by weight of the compositions of the present invention.

Additional Ingredients

A variety of additional ingredients can be incorporated into the compositions of the present invention. Non-limiting examples of these additional ingredients include vitamins and derivatives thereof (e.g tocopherol, tocopherol acetate, and the like); other thickening agents (e.g., polyacrylamide and $C_{13-14}$ isoparaffin and laureth-7, available as Sepigel 305 from Seppic Corp., Fairfield, N.J.; and branched polysaccharides such as scleroglucan available under the tradename Clearogel CS 11 from Michel Mercier Products Inc., Mountainside, N.J.); acrylic acid homopolymers crosslinked with an allyl ether of pentaerythritol or an allyl ether of sucrose which are known by the CTFA designation of carbomer and are commercially available from B. F. Goodrich under the Carbopol trademark; and copolymers of C10–30 alkyl acrylates with acrylic acid, alkyl esters of acrylic acid, methacrylic acid, alkyl esters of methacrylic acid, crosslinked with an allyl ether of sucrose or an allyl ether of pentaerythritol, which are known by the CTFA designation acrylates/C10–30 alkyl acrylate crosspolymer, and are commericially available as Carbopol 1342, Pemulen TR-1, and Pemulen TR-2, from B. F. Goodrich); resins; gums (e.g. guar gum, xanthan gum and the like); waxes (both naturally occurring and synthetic); polymers for aiding the film-forming properties and substantivity of the composition (such as a copolymer of eicosene and vinyl pyrrolidone, an example of which is available from GAF Chemical Corporation as Ganex V-220$_R$); abrasive scrub particles for cleansing and exfoliating the skin [e.g., ACuscrub Mild Abrasives (e.g., ACuscrub 30, 31, 32, 40, 41, 42, 43, 44, 50, 51, and 52) available from Allied Signal, Inc., Morristown, N.J.; and 3M Brand PMU Capsules microecapsulated mineral oil available from 3M Corporation, St. Paul, Minn.]; preservatives for maintaining the antimicrobial integrity of the compositions; skin penetration aids such as DMSO, 1-dodecylazacycloheptan-2-one (available as Azone from the Upjohn Co.) and the like; artificial tanning ingredients and tan accelerators such as dihydroxyacetone, tyrosine, tyrosine esters such as ethyl tyrosinate, and phospho-DOPA); skin bleaching (or lightening) agents including but not limited to hydroquinone, kojic acid and sodium metabisulfite; antioxidants; chelators and sequestrants; and aesthetic components such as fragrances, pigments, colorings, essential oils, skin sensates, astringents, skin soothing agents, skin healing agents and the like, nonlimiting examples of these aesthetic components include panthenol and derivatives (e.g. ethyl panthenol), aloe vera, pantothenic acid and its derivatives, clove oil, menthol, camphor, eucalyptus oil, eugenol, menthyl lactate, witch hazel distillate, allantoin, bisabalol, dipotassium glycyrrhizinate and the like.

Methods for Cleansing the Skin and Depositing an Active Upon the Skin Surface

The emulsion compositions of the present invention are useful for cleansing the skin and also for depositing an active ingredient onto the skin during the cleansing process. Typically, a suitable amount of the cleansing composition is applied to the skin to be cleansed. It is preferred to pre-moisten the skin with water. Alternatively, a suitable amount of the cleansing composition can be applied to the skin via intermediate application to a washcloth, a sponge, or other application device. It has been found that the compositions of the present invention provide their optimal cleansing performance when combined with water during the cleansing process. To complete the cleansing process, the composition is thoroughly rinsed from the skin with water, leaving the active ingredient on the skin surface. To cleanse the skin and deposit an active, an effective amount of the emulsion composition is utilized. Generally an effective amount of emulsion will depend upon the needs and usage habits of the individual. Nonlimiting effective amounts range from about 0.5 mg/cm$^2$ to about 5.0 mg/cm$^2$ of skin area to be cleansed.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLES I–V

Cleansing Products Containing Salicylic Acid

A cleansing emulsion containing salicylic acid is prepared by combining the following ingredients using conventional mixing techniques.

| | % Weight/Weight | | | | |
|---|---|---|---|---|---|
| Ingredient | I | II | III | IV | V |
| Water | QS 100 | QS 100 | QS 100 | QS 100 | QS 100 |
| PPG-14 Butyl Ether | 6.00 | 7.00 | 0 | 7.00 | 6.00 |
| PPG-10 Butanediol | 0 | 0 | 6.00 | 0 | 0 |
| Glycerin | 3.00 | 3.00 | 3.00 | 3.00 | 3.00 |
| Salicylic Acid | 2.00 | 2.00 | 2.00 | 2.00 | 2.00 |
| Polyquaternium 37 (and) Mineral Oil (and) PPG-1 Trideceth[1] | 2.00 | 2.00 | 1.00 | 0 | 0 |
| Polyacrylamide and C13-14 laureth-7[2] | 0 | 0 | 0 | 0 | 2.00 |
| Stearyl Alcohol | 2.00 | 2.00 | 1.50 | 3.00 | 2.00 |
| Cetyl Alcohol | 2.00 | 2.00 | 1.50 | 3.00 | 2.00 |
| Polyolprepolymer-2[3] | 1.00 | 0.50 | 2.00 | 0.50 | 0.25 |
| PPG-30 | 1.00 | 0.50 | 0 | 0.50 | 0.25 |
| Distearyl dimethyl ammonium Chloride | 0.50 | 0.50 | 0.50 | 1.00 | 0.50 |
| Cetyl Hydroxyethyl Cellulose[4] | 0 | 0 | 0.50 | 0 | 0 |
| Urea | 0.50 | 0.50 | 0 | 0.50 | 0.50 |
| Menthol | 0.20 | 0.20 | 0 | 0.20 | 0.20 |
| Fragrance | 0.60 | 0.60 | 0.30 | 0.60 | 0.60 |
| Disodium EDTA | 0.01 | 0.01 | 0.01 | 0.01 | 0.01 |

[1]Available as Salcare SC95, from Allied Colloids (Suffolk, VA).
[2]Available as Sepigel 305 from Seppic Corporation (Fairfield, NJ).
[3]Proposed CTFA designation for poly[oxy(methyl-1,2-ethanediyl)],-alpha-hydro-omega-hydroxy-, polymer with 1,1'methylene-bis-(4-isocyanatocyclohexane), which is available as Topicare 35A from Penederm Inc. (Foster City, CA) through Barnet Product Corp. (Englewood Cliffs, NJ).
[4]Available as Natrosol CS Plus, from Aqualon Corp (Wilmington, DE).

A water phase is first prepared by combining the glycerin, disodium EDTA, the cetyl hydroxyethyl cellulose (if any), and the water (where additional water is added later in the procedure, about 98% of the water is initially used), and then heating the mixture to 75–80° C. with stirring. In a separate vessel the PPG-14 butyl ether (if any), the PPG-10 butane diol (if any), the PPG-30 (if any), and the hydroxy-terminated urethane polymer are combined with stirring to form an oil phase. Next, the salicylic is added to this oil phase which is heated to 75–80° C. with stirring. Once the salicylic has dissolved the cetyl alchol, stearyl alcohol, and distearyl dimethyl ammonium chloride are added to this oil phase with stirring. Next, the polyquaternium 37 (and) mineral oil (and) PPG-1 trideceth (if any), and the polyacrylamide and C13–14 isoparaffin and laureth-7 (if any) are added to this oil phase with stirring. Next, the emulsion is made by adding the oil phase to the water phase with stirring using a homogenizing mill. The resulting emulsion is then cooled to 40° C. while mixing. In a separate vessel the urea (if any) is dissolved in the remaining water and then added to the emulsion with stirring. The emulsion is then further cooled to 30° C. and the fragrance (if any) and menthol (if any) are added. The emulsion is then cooled to room temperature.

The resulting emulsions are useful for application to the skin for cleansing purposes. Upon rinsing from the skin, the composition delivers salicylic acid and are useful for treating acne, and also for treating wrinkles and other age-related conditions of the skin.

EXAMPLES VI–IX

Cleansing Products Containing Salicylic Acid

A cleansing emulsion containing salicylic acid is prepared by combining the following ingredients using conventional mixing techniques.

| | % Weight/Weight | | | |
|---|---|---|---|---|
| Ingredient | VI | VII | VIII | IX |
| Water | QS 100 | QS 100 | QS 100 | QS 100 |
| PPG-14 Butyl Ether | 7.00 | 3.25 | 3.25 | 3.25 |
| Glycerin | 3.00 | 3.00 | 3.00 | 3.00 |
| Salicylic Acid | 2.00 | 2.00 | 2.00 | 2.00 |
| Polyquaternium 37 (and) Mineral Oil and) PPG-1 Trideceth[1] | 1.50 | 0 | 0 | 0 |
| Behenyl Alcohol | 0 | 1.00 | 1.00 | 1.00 |
| Stearyl Alcohol | 2.00 | 1.50 | 1.50 | 2.50 |

-continued

| Ingredient | % Weight/Weight | | | |
|---|---|---|---|---|
| | VI | VII | VIII | IX |
| Cetyl Alcohol | 2.00 | 1.50 | 1.50 | 2.50 |
| Polyolprepolymer-2[2] | 0.50 | 0 | 0 | 0 |
| PPG-30 | 0.50 | 0.25 | 0.25 | 0.25 |
| Distearyl dimethyl ammonium Chloride | 0.50 | 1.00 | 1.00 | 1.00 |
| Urea | 0 | 0.50 | 0.50 | 0.50 |
| Steareth-21 | 0 | 0.50 | 0.50 | 0.50 |
| Steareth-2 | 0 | 0.25 | 0.25 | 0.25 |
| Menthol | 0.10 | 0.10 | 0.10 | 0.10 |
| Fragrance | 0.60 | 0.55 | 0.55 | 0.55 |
| Disodium EDTA | 0.01 | 0.01 | 0.01 | 0.01 |
| Abrasive Scrub Particles[3] | 0 | 0 | 1.00 | 1.00 |

[1]Available as Salcare SC95, from Allied Colloids (Suffolk, VA).
[2]Proposed CTFA designation for poly[oxy(methyl-1,2-ethanediyl)], -alpha-hydro-omega-hydroxy-, polymer with 1,1'methylene-bis-(4-isocyanatocyclohexane), which is available as Topicare 35A from Penederm Inc. (Foster City, CA) through Barnet Product Corp. (Englewood Cliffs, NJ).
[3]Available as ACurscrub 51 Mild Abrasive, from Allied Signal, Inc. (Morristown, NJ).

The emulsions are prepared using the general procedure given for Examples I–V and involves the preparation of the oil and water phases. The behenyl alcohol (if any), steareth-21 (if any), and steareth-2 (if any), are mixed with the oil phase. The abrasive scrub particles (if any), are mixed into the completed emulsion with stirring.

The resulting emulsions are useful for application to the skin for cleansing purposes. Upon rinsing from the skin, the compositions deliver salicylic acid to the skin and are useful for treating acne, and also for treating wrinkles and other age-related conditions of the skin.

EXAMPLE X

Cleansing Product Containing Ibuprofen

A cleansing emulsion containing ibuprofen is prepared by combining the following ingredients using conventional mixing techniques.

| Ingredient | % Weight/Weight |
|---|---|
| Water | QS 100 |
| PPG-14 Butyl Ether | 6.00 |
| Glycerin | 3.00 |
| Ibuprofen | 2.00 |
| Polyquaternium 37 (and) Mineral Oil (and) PPG-1 Trideceth | 2.00 |
| Stearyl Alcohol | 2.00 |
| Cetyl Alcohol | 2.00 |
| Polyolprepolymer-2 | 1.00 |
| PPG-30 | 1.00 |
| Distearyl dimethyl ammonium Chloride | 0.50 |
| Urea | 0.50 |
| Menthol | 0.20 |
| Fragrance | 0.60 |
| Disodium EDTA | 0.01 |

An emulsion is prepared using the general procedure given for Examples I–IV with the 2% salicylic acid being replaced with 2% ibuprofen.

The resulting emulsion is useful for application to the skin for cleansing purposes. Upon rinsing from the skin, the composition delivers ibuprofen to the skin and is useful for providing an anti-inflammatory benefit.

EXAMPLE XI

Cleansing Product Containing 2,4,4'-Trichloro-2'-hydroxy Diphenyl Ether

A cleansing emulsion containing 2,4,4'-trichloro-2'hydroxy diphenyl ether (i.e. triclosan) is prepared by combining the following ingredients using conventional mixing techniques.

| Ingredient | % Weight/Weight |
|---|---|
| Water | QS 100 |
| PPG-15 Stearyl Ether | 6.00 |
| Glycerin | 3.00 |
| 2,4,4'-trichloro-2'hydroxy dipheny ether | 0.50 |
| Polyquaternium 37 (and) Mineral Oil (and) PPG-1 Trideceth | 2.00 |
| Stearyl Alcohol | 2.00 |
| Cetyl Alcohol | 2.00 |
| Polyolprepolymer-2 | 1.00 |
| PPG-30 | 1.00 |
| Distearyl dimethyl ammonium Chloride | 0.50 |
| Urea | 0.50 |
| Menthol | 0.20 |
| Fragrance | 0.60 |
| Disodium EDTA | 0.01 |

An emulsion is prepared using the general procedure given for Examples I–IV with the 2% salicylic acid being replaced with 0.5% 2,4,4'-trichloro-2'hydroxy diphenyl ether.

The resulting emulsion is useful for application to the skin for cleansing purposes. Upon rinsing from the skin, the composition delivers 2,4,4'-trichloro-2'hydroxy diphenyl ether to the skin and is useful for treating acne and for providing an anti-microbial benefit.

EXAMPLE XII

Cleansing Product Containing Retinoic Acid

A cleansing emulsion containing trans-retinoic acid is prepared by combining the following ingredients using conventional mixing techniques.

| Ingredient | % Weight/Weight |
|---|---|
| Water | QS 100 |
| PPG-14 Butyl Ether | 6.00 |
| Glycerin | 3.00 |
| Trans-Retinoic Acid | 0.10 |
| Polyquaternium 37 (and) Mineral Oil (and) PPG-1 Trideceth | 2.00 |
| Stearyl Alcohol | 1.50 |
| Cetyl Alcohol | 1.50 |
| Polyolprepolymer-2 | 1.00 |
| PPG-30 | 1.00 |
| Distearyl dimethyl ammonium Chloride | 0.50 |
| Urea | 0.50 |
| Fragrance | 0.30 |
| Disodium EDTA | 0.01 |

An emulsion is prepared using the general procedure given for Examples I–IV with th 2% salicylic acid being replaced with 0.1% trans retinoic acid.

The resulting emulsion is useful for application to the skin for cleansing purposes. Upon rinsing from the skin, the composition delivers trans retinoic acid to the skin and is useful for providing treating acne, and also for treating wrinkles and other age-related conditions of the skin.

EXAMPLE XIII

Cleansing Product Containing Phenoxyisopropanol

A cleansing emulsion containing phenoxyisopropanol is prepared by combining the following ingredients using conventional mixing techniques.

| Ingredient | % Weight/Weight |
|---|---|
| Water | QS 100 |
| PPG-14 Butyl Ether | 0.50 |
| Glycerin | 3.00 |
| Phenoxyisopropanol | 6.00 |
| Polyquaternium 37 (and) Mineral Oil (and) PPG-1 Trideceth | 2.00 |
| Stearyl Alcohol | 2.00 |
| Cetyl Alcohol | 2.00 |
| Polyolprepolymer-2 | 1.00 |
| PPG-30 | 1.00 |
| Distearyl dimethyl ammonium Chloride | 0.50 |
| Urea | 0.50 |
| Menthol | 0.20 |
| Fragrance | 0.40 |
| Disodium EDTA | 0.01 |

An emulsion is prepared using the general procedure given for Examples I–IV with the 2% salicylic acid being replaced with 6% phenoxyisopropanol.

The resulting emulsion is useful for application to the skin for cleansing purposes. Upon rinsing from the skin, the composition delivers trans phenoxyisopropanol to the skin and is useful for providing treating acne, and for providing an anti-microbial benefit.

EXAMPLE XIV

Cleansing Product Containing Clotrimazole

A cleansing emulsion containing clotrimazole is prepared by combining the following ingredients using conventional mixing techniques.

| Ingredient | % Weight/Weight |
|---|---|
| Water | QS 100 |
| PPG-14 Butyl Ether | 6.00 |
| Glycerin | 3.00 |
| Clortrimazole | 1.00 |
| Polyquaternium 37 (and) Mineral Oil (and) PPG-1 Trideceth | 2.00 |
| Stearyl Alcohol | 1.50 |
| Cetyl Alcohol | 1.50 |
| Polyolprepolymer-2 | 0.50 |
| PPG-30 | 0.50 |
| Distearyl dimethyl ammonium Chloride | 0.50 |
| Urea | 0.50 |
| Disodium EDTA | 0.01 |

An emulsion is prepared using the general procedure given for Examples I–IV with the 2% salicylic acid being replaced with 1% clortrimazole.

The resulting emulsion is useful for application to the skin for cleansing purposes. Upon rinsing from the skin, the composition delivers clortrimazole to the skin and is useful for providing an anti-fungal benefit.

EXAMPLE XV

Cleansing Product Containing Sunscreens

A cleansing emulsion containing sunscreens is prepared by combining the following ingredients using conventional mixing techniques.

| Ingredient | % Weight/Weight |
|---|---|
| Water | QS 100 |
| PPG-14 Butyl Ether | 0.10 |
| Glycerin | 3.00 |
| 2-Ethylhexyl p-methoxycinnamate | 7.50 |
| Oxybenzone | 3.00 |
| Polyquaternium 37 (and) Mineral Oil (and) PPG-1 Trideceth | 2.00 |
| Stearyl Alcohol | 2.00 |
| Cetyl Alcohol | 2.00 |
| Polyolprepolymer-2 | 1.00 |
| PPG-30 | 1.00 |
| Distearyl dimethyl ammonium Chloride | 0.50 |
| Urea | 0.50 |
| Menthol | 0.20 |
| Fragrance | 0.60 |
| Disodium EDTA | 0.01 |

An emulsion is prepared using the general procedure given for Examples I–IV with the 2% salicylic acid being replaced with a mixture of 7.5% 2-ethylhexyl p-methoxycinnamate and 3% oxybenzone.

The resulting emulsion is useful for application to the skin for cleansing purposes. Upon rinsing from the skin, the composition delivers 2-ethylhexyl p-methoxycinnamate and oxybenzone to the skin and is useful for providing protection from the sun's ultraviolet rays.

What is claimed is:

1. An oil-in-water emulsion composition useful for personal cleansing, comprising:

(a) from about 0.05% to about 20% of an active ingredient having a solubility parameter from about 7 to about 13;

(b) from about 0.1% to about 25% of an alkoxylated ether of the formula

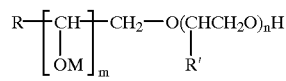

wherein R is selected from the group consisting of H and $C_1$–$C_{30}$ straight chain or branched chain alkyl, m is an integer from 0 to about 6, R' is selected from the group consisting of methyl and ethyl, and n is an integer form about 3 to about 30; or an alkoxylated diether of the formula:

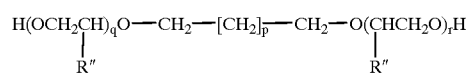

wherein R" is selected from the group consisting of methyl and ethyl, p is an integer from about 1 to about 6, and each q and r are independently selected so that their sum is an integer from about 3 to about 30;

(c) from about 0.05% to about 10% of a cationic emulsifier, wherein the cationic emulsifier is a cationic ammonium salt having the formula:

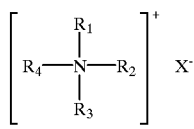

wherein R1 is $R_5CO-(CH_2)_n-$, wherein R5 is an alkyl group having from about 12 to about 22 carbon atoms, and n is an integer from about 2 to about 6; R2, R3, and R4 are independently selected from hydrogen, an alkyl group having from about 1 to about 22 carbon atoms, or aromatic, aryl or alkaryl groups having from about 12 to about 22 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof;
(d) from about 0% to about 10% of a deposition aiding polymer;
(e) from about 0% to about 10% of a polymeric thickener; and
(f) from about 25% to about 99.7% water
wherein the active is deposited on the skin during the cleansing process.

2. An emulsion composition according to claim 1 wherein said active is selected from the group consisting of salicylic acid, cis-retinoic acid, trans-retinoic acid, azelaic acid, erythromycin, resorcinol, ibuprofen, naproxen, hydrocortisone, phenoxyethanol, phenoxypropanol, phenoxyisopropanol, 2,4,4'-trichloro-2'-hydroxy diphenyl ether, 3,4,4'-trichlorocarbanilide, 2-ethylhexyl p-methoxycinnamate, 2-ethylhexyl N,N-dimethyl-p-aminobenzoate, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, 4-N,N-(2-ethylhexyl)-methylaminobenzoic acid ester of 4-(2-hydroxyethoxy) dibenzoylmethane, and mixtures thereof.

3. An emulsion composition according to claim 2 wherein said emulsifier is a cationic ammonium salt having the formula:

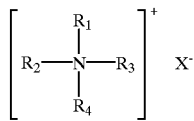

wherein $R_1$ is an alkyl group having from about 12 to about 22 carbon atoms, $R_2$ is H or an alkyl group having from about 1 to about 22 carbon atoms, $R_3$ and $R_4$ are independently selected from H or an alkyl group having from about 1 to about 3 carbon atoms, and X is an anion selected from chloride, bromide, iodide, acetate, phosphate, nitrate, sulfate, methyl sulfate, ethyl sulfate, tosylate, lactate, citrate, glycolate, and mixtures thereof.

4. An emulsion composition according to claim 3 wherein said deposition aiding polymer is selected from the group consisting of hydroxy-terminated urethane polymers, polypropylene glycols, and mixtures thereof.

5. An emulsion composition according to claim 4 wherein said hydroxy-terminated urethane polymer is of the formula:

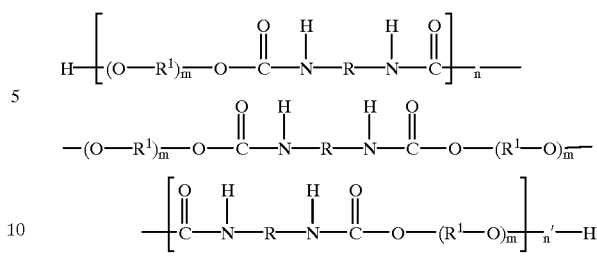

wherein R represents an alkyl or alkenyl radical having from about one to about 20 carbon atoms, or a cycloalkyl or cycloalkyneyl radical containing from about 5 to about 10 carbon atoms, or a mononuclear or fused ring aryl radical containing from about 6 to about 10 carbon atoms, unsubstituted or substituted with one or more C1–C6 alkyl, C1–C6 alkoxy, C1–C6 alkoxy-substituted C1–C6, nitro or amino groups or halogen atoms; $R^1$ is the same or different alkyl or akenyl radical; m is an integer selected so at to provide an $(O-R^1)$ moiety having a molecular weight of from about 40 to about 6000; and n and n' are the same or different integers of from 0 to about 30 inclusive, correlated with m so as to provide a hydroxy-terminated urethane compound having a molecular weight from about 220 to about 37,000.

6. An emulsion composition according to claim 4 wherein said polypropylene glycol is of the formula:

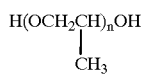

wherein n is an integer from about 10 to about 50.

7. An emulsion composition according to claim 5 wherein said alkoxylated ether or alkoxyated diether is selected from the group consisting of PPG-10 butyl ether, PPG-11 butyl ether, PPG 12 butyl ether, PPG-13 butyl ether, PPG-14 butyl ether, PPG 15 butyl ether, PPG-16 butyl ether, PPG-17 butyl ether, PPG-18 butyl ether, PPG-19 butyl ether, PPG-20 butyl ether, PPG-22 butyl ether, PPG-24 butyl ether, PPG-30 butyl ether, PPG-11 stearyl ether, PPG-15 stearyl ether, PPG-10 oleyl ether, PPG-7 lauryl ether, PPG-30 isocetyl ether, PPG-10 glyceryl ether, PPG-15 glyceryl ether, PPG-10 butylene glycol ether, PPG-15 butylene glycol ether, PPG-27 glyceryl ether, PPG-30 cetyl ether, PPG-28 cetyl ether, PPG-10 cetyl ether, PPG-10 hexylene glycol ether, PPG-15 hexylene glycol ether, PPG-10 1,2,6-hexanetriol ether, PPG-15 1,2,6-hexanetriol ether, PPG-10 1,4-butanediol diether, PPG-12 1,4-butanediol diether, PPG-14 1,4-butanediol diether, PPG-2 butanediol diether, PPG-10 1,6-hexanediol diether, PPG-12 1,6-hexanediol diether, PPG-14 hexanediol diether, PPG-20 hexanediol diether, and mixtures thereof.

8. An emulsion composition according to claim 7 wherein said alkoxylated ether or alkoxylated diether is selected from the group consisting of PPG-14 butyl ether, PPG-15 stearyl ether, PPG-11 stearyl ether, PPG-20 oleyl ether, PPG-10 1,4-butanediol diether, PPG-12 1,4-butanediol diether, PPG-10 1,6-hexandiol diether, and PPG-12 hexanediol diether, and mixtures thereof.

9. An emulsion composition according to claim 8 wherein said alkoyxlated ether or alkoxylated diether is selected from the group consisting of PPG-14 butyl ether, PPG-15 stearyl ether, PPG-10 1,4-butanediol diether, and mixtures thereof.

10. An emulsion composition according to claim 9 wherein said cationic emulsifier is selected from the group consisting of dilauryl dimethyl ammoniun chloride, distearyl dimethyl ammonium chloride, dimyristyl dimethyl ammonium chloride, dipalmityl dimethyl ammonium chloride, and mixtures thereof.

11. An emulsion composition according to claim 10 wherein said polymeric thickener is selected from the group consisting of crosslinked polyacrylate polymers, alkyl hydroxyalkylcellulose ethers, quaternary ammonium hydroxyalkylcellulose polymers, and mixtures thereof.

12. An emulsion composition according to claim 11 wherein said crosslinked polyacrylate polymer is a polymer comprising the monomer units $(A)_l$, $(B)_m$, $(C)_n$, and a crosslinking agent, wherein (A) is a dialkylaminoalkyl acrylate monomer or its quaternary ammonium or acid addition salt thereof, (B) is a dialkylaminoalkyl methacrylate monomer or its quaternary ammonium or acid addition salt thereof, (C) is a nonionic monomer polymerizable with (A) or (B), and l, m, and n are independently zero or greater, but at least one of l and m is one or greater.

13. An emulsion composition according to claim 12 wherein said crosslinking agent is methylenebisacrylamide.

14. An emulsion composition according to claim 11 wherein said alkylhydroxyalcellulose ether is cetyl hydroxyethylcellulose.

15. An emulsion composition according to claim 11 wherein said quaternary ammonium hydroxyalkylcellulose polymer is selected from the group consisting of polyquaternium-24, laurdimonium hydroxyethyl cellulose, steardimonium hydroxethyl cellulose, cocodimonium hydroxyethyl cellulose, and mixtures thereof.

16. An emulsion composition according to claim 13 which further comprises from about 0.1% to about 10% of a fatty alcohol.

17. An emulsion composition according to claim 16 wherein said fatty alcohol is selected from the group consisting of lauryl alcohol, myristyl alcohol, cetyl alcohol, stearyl alcohol, isostearyl alcohol, oleyl alcohol, linoleyl alcohol, linolenyl alcohol, ricinoleyl alcohol, behenyl alcohol, and mixtures thereof.

18. An emulsion composition according to claim 17 which further comprises from about 1% to about 5% of a humectant.

19. An emulsion composition according to claim 18 wherein said humectant is selected from the group consisting of urea, glycerin, propoxylated glycerin, butylene glycol, diplropylene glycol, tripropylene glycol, hexylene glycol and mixtures thereof.

20. An emulsion composition according to claim 19 which further comprises from about 1% to about 10% of an emollient selected from the group consisting of volatile silicone oils, non-volatile silicone oils, highly branched hydrocarbons, and mixtures thereof.

21. An emulsion composition according to claim 3 wherein said emulsifier further comprises a mixture of a high HLB nonionic emulsifer and a low HLB nonionic emulsifier.

22. An emulsion composition according to claim 21 wherein said high HLB nonionic emulsifier is selected from the group consisting of ceteth-10, steareth-21, and mixtures thereof, and said low HLB nonionic emulsifier is selected from the group consisting of steareth-2, cetheth-2, laureth-2, and mixtures thereof.

23. An emulsion composition according to claim 22 wherein said deposition aiding polymer is a polypropylene glycol of the formula:

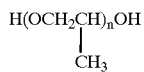

wherein n is an integer from about 10 to about 50.

24. An oil-in-water emulsion composition useful for personal cleansing, comprising:
(a) from about 0.05% to about 20% of salicylic acid;
(b) from about 0.1% to about 25% of an alkoxylated ether of the formula

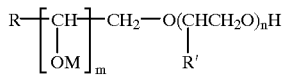

wherein R is selected from the group consisting of H and C1–C30 straight chain or branched chain alkyl, m is an integer from 0 to about 6, R' is selected from the group consisting of methyl and ethyl, and n is an integer from about 3 to about 30; or an alkoxylated diether of the formula

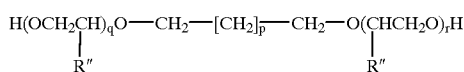

wherein R" is selected from the group consisting of methyl and ethyl, p is an integer from about 1 to about 6, and each q and r are independently selected so that their sum is an integer from about 3 to about 30;
(c) from about 0.05% to about 10% of a cationic emulsifier, wherein the cationic emulsifier is a cationic ammonium salt having the formula:

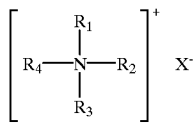

wherein R1 is $R_5CO—(CH2)_n—$, wherein R5 is an alkyl group having from about 12 to about 22 carbon atoms, and n is an integer from about 2 to about 6: R2, R3, and R4 are independently selected from hydrogen, an alkyl group having from about 1 to about 22 carbon atoms, or aromatic, aryl or alkaryl groups having from about 12 to about 22 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof;
(d) from 0% to about 10% of a deposition aiding polymer;
(e) from 0% to about 10% of a polymeric thickener; and
(f) from about 25% to about 99.7% water;
wherein the active is deposited on the skin during the cleansing process and wherein said composition has a pH from about 2 to about 7.

25. An emulsion composition according to claim 24 having a pH from about 2.5 to about 5.

26. An emulsion composition according to claim 25 having a pH from about 2.5 to about 4.

27. An emulsion composition according to claim 26 having a pH from about 2.5 to about 3.

28. An emulsion composition according to claim 27 wherein said emulsifier is a cationic ammonium salt having the formula:

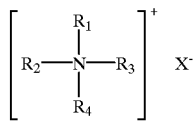

wherein $R_1$ is an alkyl group having from about 12 to about 22 carbon atoms, $R_2$ is H or an alkyl group having from about 1 to about 22 carbon atoms, $R_3$ and $R_4$ are independently selected from H or an alkyl group having from about 1 to about 3 carbon atoms, and X is an anion selected from chloride, bromide, iodide, acetate, phosphate, nitrate, sulfate, methyl sulfate, ethyl sulfate, tosylate, lactate, citrate, glycolate, and mixtures thereof.

29. An emulsion composition according to claim 26 wherein said deposition aiding polymer is selected from the group consisting of hydroxy-terminated urethane polymers, polypropylene glycols, and mixtures thereof.

30. An emulsion composition according to claim 29 wherein said hydroxy-terminated urethane polymer is of the formula:

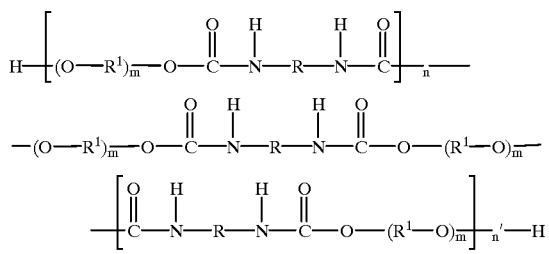

wherein R represents an alkyl or alkenyl radical having from about one to about 20 carbon atoms, or a cycloalkyl or cycloalkyneyl radical containing from about 5 to about 10 carbon atoms, or a mononuclear or fused ring aryl radical containing from about 6 to about 10 carbon atoms, unsubstituted or substituted with one or more C1–C6 alkyl, C1–C6 alkoxy, C1–C6 alkoxy-substituted C1–C6, nitro or amino groups or halogen atoms; $R^1$ is the same or different alkyl or akenyl radical; m is an integer selected so at to provide an ($O-R^1$) moiety having a molecular weight of from about 40 to about 6000; and n and n' are the same or different integers of from 0 to about 30 inclusive, correlated with m so as to provide a hydroxy-terminated urethane compound having a molecular weight from about 220 to about 37,000.

31. An emulsion composition according to claim 29 wherein said polypropylene glycol is of the formula:

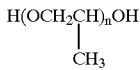

wherein n is an integer from about 10 to about 50.

32. An emulsion composition according to claim 30 wherein said polymeric thickener is selected from the group consisting of crosslinked polyacrylate polymers, alkyl hydroxyalkylcellulose ethers, quaternary ammonium hydroxyalkylcellulose polymers, and mixtures thereof.

33. An emulsion composition according to claim 32 wherein said crosslinked polyacrylate polymer is a polymer comprising the monomer units $(A)_l$, $(B)_m$, $(C)_n$, and a crosslinking agent, wherein (A) is a dialkylaminoalkyl acrylate monomer or its quaternary ammonium or acid addition salt thereof, (B) is a dialkylaminoalkyl methacrylate monomer or its quaternary ammonium or acid addition salt thereof, (C) is a nonionic monomer polymerizable with (A) or (B), and l, m, and n are independently zero or greater, but at least one of l and m is one or greater.

34. An emulsion composition according to claim 33 wherein said crosslinking agent is methylenebisacrylamide.

35. An emulsion composition according to claim 28 wherein said emulsifier further comprises a mixture of a high HLB nonionic emulsifer and a low HLB nonionic emulsifier.

36. An emulsion composition according to claim 35 wherein said high HLB nonionic emulsifier is selected from the group consisting of ceteth-10, steareth-21, and mixtures thereof, and said low HLB nonionic emulsifier is selected from the group consisting of steareth-2, cetheth-2, laureth-2, and mixtures thereof.

37. An emulsion composition according to claim 36 wherein said deposition aiding polymer is a polypropylene glycol of the formula:

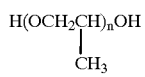

wherein n is an integer from about 10 to about 50.

38. An oil-in-water emulsion composition useful for personal cleansing, comprising:

(a) from about 0.05% to about 20% of an active ingredient having a solubility parameter from about 7 to about 13;

(b) from about 0.1% to about 25% of an alkoxylated ether of the formula

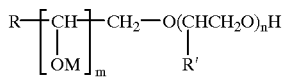

wherein R is selected from the group consisting of H and C1–C30 straight chain or branched chain alkyl, m is an integer from 0 to about 6, R' is selected from the group consisting of methyl and ethyl, and n is an integer from about 3 to about 30; or an alkoxylated diether of the formula

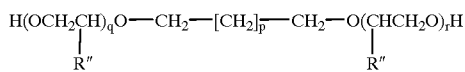

wherein R" is selected from the group consisting of methyl and ethyl, p is an integer from about 1 to about 6, and each q and r are independently selected so that their sum is an integer from about 3 to about 30;

(c) from about 0.05% to about 10% of a cationic emulsifier, wherein the cationic emulsifier is a cationic ammonium salt having the formula:

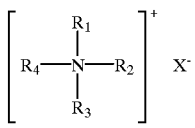

wherein R1 is $R_5CO-(CH2)_n-$, wherein R5 is an alkyl group having from about 12 to about 22 carbon atoms, and n is an integer from about 2 to about 6; R2 R3, and R4 are independently selected from hydrogen, an alkyl group having from about 1 to about 22 carbon atoms, or aromatic, aryl or alkaryl groups having from about 12 to about 22 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof;

(d) from about 0.1% to about 10% of a deposition aiding polymer which is a mixture of a hydroxy-terminated urethane polymer and a polypropylene glycol wherein the weight/weight ratio of said hydroxy-terminated urethane polymer to said polypropylene glycol is from about 1:1.5 to about 1.5:1;

(e) from 0% to about 10% of a polymeric thickener, and (f) from about 25% to about 99.7% water wherein the active is deposited on the skin during the cleansing process.

39. An emulsion composition according to claim 38 wherein said hydroxy-terminated urethane polymer is of the formula:

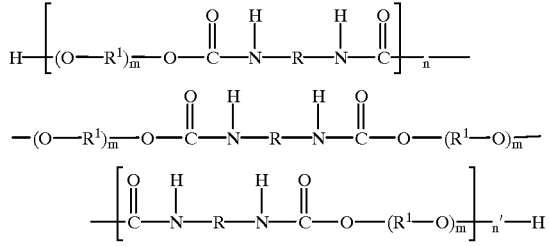

wherein R represents an alkyl or alkenyl radical having from about one to about 20 carbon atoms, or a cycloalkyl or cycloalkyneyl radical containing from about 5 to about 10 carbon atoms, or a mononuclear or fused ring aryl radical containing from about 6 to about 10 carbon atoms, unsubstituted or substituted with one or more C1–C6 alkyl, C1–C6 alkoxy, C1–C6 alkoxy-substituted C1–C6, nitro or amino groups or halogen atoms; $R^1$ is the same or different alkyl or akenyl radical; m is an integer selected so at to provide an $(O-R^1)$ moiety having a molecular weight of from about 40 to about 6000; and n and n' are the same or different integers of from 0 to about 30 inclusive, correlated with m so as to provide a hydroxy-terminated urethane compound having a molecular weight from about 220 to about 37,000; and wherein said polypropylene glycol is of the formula:

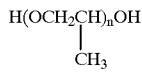

wherein n is an integer from about 10 to about 50.

40. An emulsion composition according to claim 39 wherein said active is selected from the group consisting of salicylic acid, cis-retinoic acid, trans-retinoic acid, azelaic acid, erythromycin, resorcinol, ibuprofen, naproxen, hydrocortisone, phenoxyethanol, phenoxypropanol, phenoxyisopropanol, 2,4,4'-trichloro-2'-hydroxy diphenyl ether, 3,4,4'-trichlorocarbanilide, 2-ethylhexyl p-methoxycinnamate, 2-ethylhexyl N,N-dimethyl-p-aminobenzoate, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, 4-N,N-(2-ethylhexyl)-methylaminobenzoic acid ester of 4-(2-hydroxyethoxy) dibenzoylmethane, and mixtures thereof.

41. An emulsion composition according to claim 40 wherein said emulsifier is a cationic ammonium salt having the formula:

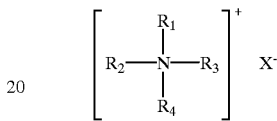

wherein $R_1$ is an alkyl group having from about 12 to about 22 carbon atoms, $R_2$ is H or an alkyl group having from about 1 to about 22 carbon atoms, $R_3$ and $R_4$ are independently selected from H or an alkyl group having from about 1 to about 3 carbon atoms, and X is an anion selected from chloride, bromide, iodide, acetate, phosphate, nitrate, sulfate, methyl sulfate, ethyl sulfate, tosylate, lactate, citrate, glycolate, and mixtures thereof.

42. An emulsion composition according to claim 41 wherein said alkoxylated ether or alkoxyated diether is selected from the group consisting of PPG-10 butyl ether, PPG-11 butyl ether, PPG 12 butyl ether, PPG-13 butyl ether, PPG-14 butyl ether, PPG 15 butyl ether, PPG-16 butyl ether, PPG-17 butyl ether, PPG-18 butyl ether, PPG-19 butyl ether, PPG-20 butyl ether, PPG-22 butyl ether, PPG-24 butyl ether, PPG-30 butyl ether, PPG-11 stearyl ether, PPG-15 stearyl ether, PPG-10 oleyl ether, PPG-7 lauryl ether, PPG-30 isocetyl ether, PPG-10 glyceryl ether, PPG-15 glyceryl ether, PPG-10 butylene glycol ether, PPG-15 butylene glycol ether, PPG-27 glyceryl ether, PPG-30 cetyl ether, PPG-28 cetyl ether, PPG-10 cetyl ether, PPG-10 hexylene glycol ether, PPG-15 hexylene glycol ether, PPG-10 1,2,6-hexanetriol ether, PPG-15 1,2,6-hexanetriol ether, PPG-10 1,4-butanediol diether, PPG-12 1,4-butanediol diether, PPG-14 1,4-butanediol diether, PPG-2 butanediol diether, PPG-10 1,6-hexanediol diether, PPG-12 1,6-hexanediol diether, PPG-14 hexanediol diether, PPG-20 hexanediol diether, and mixtures thereof.

43. An emulsion composition according to claim 42 wherein said polymeric thickener is selected from the group consisting of crosslinked polyacrylate polymers, alkyl hydroxyalkylcellulose ethers, quaternary ammonium hydroxyalkylcellulose polymers, and mixtures thereof.

44. An emulsion composition according to claim 43 wherein said crosslinked polyacrylate polymer is a polymer comprising the monomer units $(A)_l$, $(B)_m$, $(C)_n$, and a crosslinking agent, wherein (A) is a dialkylaminoalkyl acrylate monomer or its quaternary ammonium or acid addition salt thereof, (B) is a dialkylaminoalkyl methacrylate monomer or its quaternary ammonium or acid addition salt thereof, (C) is a nonionic monomer polymerizable with (A) or (B), and l, m, and n are independently zero or greater, but at least one of l and m is one or greater.

45. An emulsion composition according to claim 44 wherein said crosslinking agent is methylenebisacrylamide.

46. An emulsion composition according to claim 43 wherein said alkylhydroxyalcellulose ether is cetyl hydroxyethylcellulose.

47. An emulsion composition according to claim 43 wherein said quaternary ammonium hydroxyalkylcellulose polymer is selected from the group consisting of polyquaternium-24, laurdimonium hydroxyethyl cellulose, steardimonium hydroxethyl cellulose, cocodimonium hydroxyethyl cellulose, and mixtures thereof.

48. An emulsion composition according to claim 45 wherein said active is salicylic acid and wherein the emulsion has a pH from about 2 to about 7.

49. An emulsion compostion according to claim 48 wherein said emulsion has a pH form about 2.5 to about 3.

50. An emulsion composition according to claim 41 wherein said emulsifier further comprises a mixture of a high HLB nonionic emulsifer and a low HLB nonionic emulsifier.

51. An emulsion composition according to claim 50 wherein said high HLB nonionic emulsifier is selected from the group consisting of ceteth-10, steareth-21, and mixtures thereof, and said low HLB nonionic emulsifier is selected from the group consisting of steareth-2, cetheth-2, laureth-2, and mixtures thereof.

52. A method for cleansing skin and depositing an active upon the surface of the skin, said method comprising topically applying and subsequently rinsing from the skin an effective amount of a composition according to claim 1.

53. A method for cleansing skin and depositing an active upon the surface of the skin, said method comprising topically applying and subsequently rinsing from the skin an effective amount of a composition according to claim 24.

54. A method for cleansing skin and depositing an active upon the surface of the skin, said method comprising topically applying and subsequently rinsing from the skin an effective amount of a composition according to claim 38.

* * * * *